(12) United States Patent
van Beusechem et al.

(10) Patent No.: US 8,052,965 B2
(45) Date of Patent: Nov. 8, 2011

(54) VIRUSES WITH ENHANCED LYTIC POTENCY

(75) Inventors: Victor Willem van Beusechem, Amsterdam (NL); Willem-Ronald Gerritsen, Uithoorn (NL)

(73) Assignee: Vereniging Voor Christelijk Hoger Onderwijs, Wetenschappelijk Onderzoek en Patientenzorg, Amsterdam (NL)

( * ) Notice: Subject to any disclaimer, the term of this patent is extended or adjusted under 35 U.S.C. 154(b) by 0 days.

(21) Appl. No.: 10/501,407

(22) PCT Filed: Jan. 14, 2003

(86) PCT No.: PCT/EP03/00340
§ 371 (c)(1),
(2), (4) Date: Mar. 25, 2005

(87) PCT Pub. No.: WO03/057892
PCT Pub. Date: Jul. 17, 2003

(65) Prior Publication Data
US 2005/0220765 A1 Oct. 6, 2005

(30) Foreign Application Priority Data
Jan. 14, 2002 (EP) .................................... 02075108

(51) Int. Cl.
A61K 48/00 (2006.01)
C12N 7/00 (2006.01)
C12N 15/861 (2006.01)
(52) U.S. Cl. ...................... 424/93.2; 435/456; 435/235.1
(58) Field of Classification Search .......................... None
See application file for complete search history.

(56) References Cited

U.S. PATENT DOCUMENTS

| 5,932,210 | A | 8/1999 | Gregory et al. | |
|---|---|---|---|---|
| 6,638,762 | B1 * | 10/2003 | Chang et al. | 435/320.1 |
| 6,824,771 | B1 * | 11/2004 | Curiel et al. | 424/93.2 |
| 2002/0187126 | A1 * | 12/2002 | Blaho et al. | 424/93.2 |

FOREIGN PATENT DOCUMENTS

| WO | WO 95/12660 | 5/1995 |
|---|---|---|
| WO | WO 97/30732 | 8/1997 |
| WO | WO 98/01563 | 1/1998 |
| WO | WO 98/46779 | 10/1998 |
| WO | WO 98/46781 | 10/1998 |
| WO | WO 00/29573 | 5/2000 |
| WO | WO 00/71078 A2 | 11/2000 |
| WO | WO 01/05437 A2 | 1/2001 |
| WO | WO 01/44280 A2 | 6/2001 |
| WO | WO 01/74403 A1 | 10/2001 |

OTHER PUBLICATIONS

Debbas and White, Genes Dev. 1993, 7:546-54.*
Querido et al. Genes and Dev. 2001. 15:3104-3117.*
Fueyo et al. Oncogene 2000. 19:2-12.*
Nevins. Human Molecular Genetics. 2001. 10(7):699-703.*
Bressac et al. 1990. PNAS 87:1973-1977.*
Lin et al. Cancer Research 60, 5895-5901, Oct. 15, 2000.*
Moore et al. PNAS. 1996. p. 11295-11301.*
Hallenbeck et al (Human Gene Therapy. 1999; 10:1721-1733).*
Of Xu et al. (Human Gene Therapy. 1997; 8:177-185).*
V.W. Van Beusechem, P.B. Van Den Doel, W.R. Gerritsen, Conditionally replicative adenovirus expressing degradation-resistant p53 for enhanced oncolysis of human concer cell overexpressing murine double minute 2, Mol Cancer Ther 2005;4(6). Jun. 2005, pp. 1013-1018.
Querido E. et al., Accumulation of P53 Induced by the Adenovirus E1A Protein Requires Regions Involved in the Stimulation of DNS Synthesis, Journal of Virology, The American Society for Microbiology, US, vol. 71, No. 5, May 1997, pp. 3526-3533.
P.Yew, X. Liu, A. Berk, Adenovirus E1B Oncoprotein Tethers a Transcriptional Repression Domain to p53, Genes and Development, Cold Spring Harbor, NY, US, vol. 8 No. 2, 1994, pp. 190-202.
Teodoro J G et al, Adenovirus E1A Proteins induce apoptosis by Both P53-dependent and P53-independent mechanisms, Oncogene, Basingstoke, Hants, GB, vol. 11, No. 3, Aug. 3, 1995, pp. 467-474.
Querido et al., Regulation of P53 Levels by the E1B 55—Kilodalton protein and E4orf6 in Adenovirus-Infected Cells, Journal of Virology, the American Society for Microbiology, US, vol. 71, No. 5, May 1, 1997, pp. 3788-3798.
Tsunoda H. et al., Effects of Wild-Type and Mutated P53 and ID Proteins on the Induction of Apoptosis by Adenovirus E1A, c-Myc, Bax and Nip3 in p53 Null Mouse Cerebellum Cells, Biochemical and Biophysical *Research Communicationsm Academic Press Inc*, Orlando, FL, US vol. 255, No. 3, 1999, pp. 722-730.
Beusechem et al., Conditionally Replicative Adenovirus Expressing p53 Exhibits Enhanced Oncolytic Potency, Cancer Research, vol. 62, pp. 6165-6171, Nov. 1, 2002.
Turnell et al., "The Replicative Capacities of Large E1B-Null Group A and Group C Adenoviruses are Independent of Host Cell p53 Status", Journal of Virology, vol. 73, No. 3, pp. 2074-2083 (1999).ell p53 Status, Journal of Virology, vol. 73, No. 3, pp. 2074-2083 (1999).
Goodrum et al. "p53 Status Does Not Determine Outcome of E1B 55-Kilodalton Mutant Adenovirus Lytic Infection", Journal of Virology, vol. 72, No. 12, pp. 9479-9490 (1998).
Ridgway et al., "p53/E1b58kDa Complex Regulates Adenovirus Replication", Journal of Virology, vol. 237, pp. 404-413 (1997).
Dix et al., "Efficient Induction of Cell Death by Adenoviruses Requires Binding of E1B55k and p53", Cancer Research, vol. 60, pp. 2666-2672, (2000).
Hermiston et al., "Armed therapeutic viruses: Strategies and challenges to arming oncolytic viruses with therapeutic genes," Cancer Gene Therapy (2002) 9, 1022-1035.

* cited by examiner

*Primary Examiner* — Scott Long
(74) *Attorney, Agent, or Firm* — Hoffmann & Baron, LLP

(57) ABSTRACT

Described is a replication competent recombinant virus, being capable to replicate and having lytic capacity in target cells, the said cell being hampered in the p53 dependent apoptosis pathway, the virus including in the genome thereof, the coding sequence of at least one restoring factor functional in restoring the p53 apoptosis pathway in the said target cells, operably linked to one or more expression control sequences, functional in the said target cells, as well as the use thereof in the preparation of a medicament, in particular for suppressing uncontrolled cell growth.

20 Claims, 12 Drawing Sheets

Figure 6
MOI: 100  10  1  0.1 0.01  0 pfu/cell
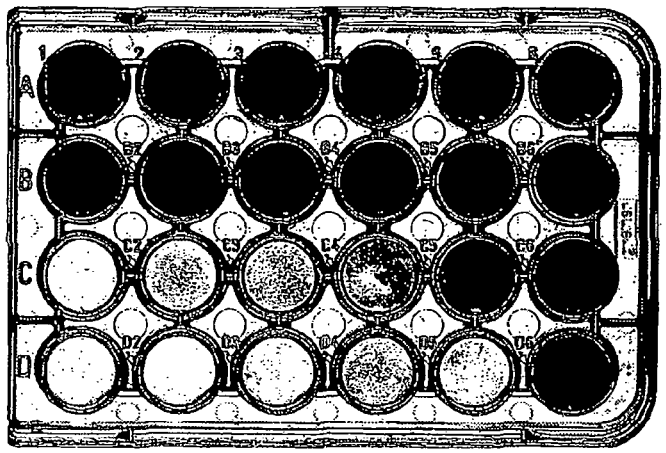
A
AdGFP
Adp53
AdΔ24
AdΔ24-p53
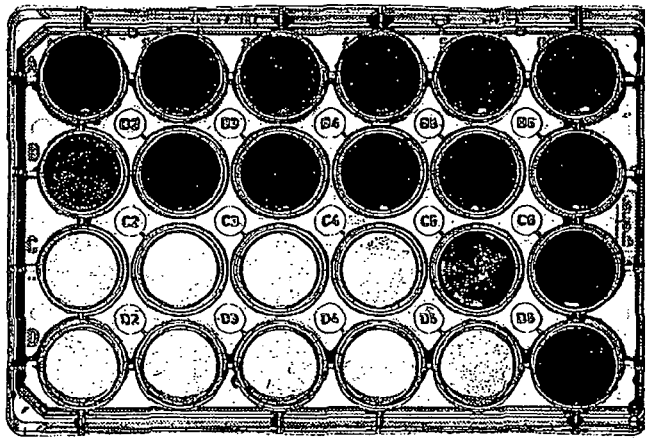
B
AdGFP
Adp53
AdΔ24
AdΔ24-p53
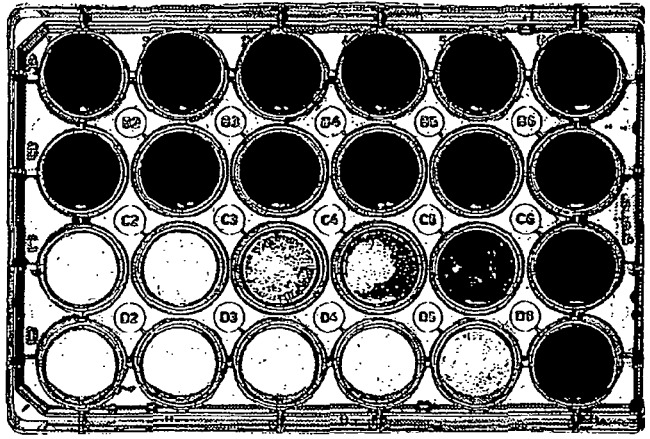
C
AdGFP
Adp53
AdΔ24
AdΔ24-p53

```
                           SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Primer for creating PCR amplification products

<400> SEQUENCE: 1
cgtttcccgt tgaatatggc                                                   20

<210> SEQ ID NO 2
<211> LENGTH: 31
<212> TYPE: DNA
<213> ORGANISM: Artificial Sequence
<220> FEATURE:
<223> OTHER INFORMATION: Primer for creating PCR amplification products

<400> SEQUENCE: 2
ctgaacatgt ttcctgactc tgagggggct c                                      31

<210> SEQ ID NO 3
<211> LENGTH: 28
<212> TYPE: DNA
<213> ORGANISM: Artificial Sequence
<220> FEATURE:
<223> OTHER INFORMATION: Primer for creating PCR amplification products

<400> SEQUENCE: 3
cctcagagtc aggaaacatg ttcagacc                                          28

<210> SEQ ID NO 4
<211> LENGTH: 20
<212> TYPE: DNA
<213> ORGANISM: Artificial Sequence
<220> FEATURE:
<223> OTHER INFORMATION: Primer for creating PCR amplification products

<400> SEQUENCE: 4
gaagtctcat ggaagccagc                                                   20

<210> SEQ ID NO 5
<211> LENGTH: 8
<212> TYPE: PRT
<213> ORGANISM: Adenovirus

<400> SEQUENCE: 5

Leu Thr Cys His Glu Ala Gly Phe
1               5
```

VIRUSES WITH ENHANCED LYTIC POTENCY

TECHNICAL FIELD OF THE INVENTION

The present invention relates to the fields of genetic modification, biotechnology and medicine. In particular, the invention provides replication competent recombinant adenoviruses with an enhanced potency to lyse cells in which they replicate. As a result, the adenoviruses of the invention replicate faster within a population of cells. The invention thus provides efficient production of recombinant adenoviruses and of factors, such as proteins, encoded by said recombinant adenoviruses, as well as efficient means to eradicate certain populations of cells. The invention finds useful applications in the areas of recombinant adenovirus production, recombinant protein production, vaccine production, and medical treatments based on removal of certain cells from a body, such as e.g. cancer cells.

DESCRIPTION OF RELATED ART

Recombinant adenoviruses are generated from the genome of adenoviruses through genetic engineering. This genetic engineering often involves insertion of heterologous DNA, including but not limited to DNA encoding a therapeutic product, into the adenovirus genome. It is to be understood, however, that the term recombinant adenovirus is also meant to include adenovirus from which parts of the virus genome have been removed without insertion of heterologous DNA. Another example of a recombinant adenovirus is a chimeric adenovirus containing parts of the genomes of different adenoviruses.

Herein, two types of recombinant adenoviruses are discriminated, i.e., replication deficient adenoviruses and replication competent adenoviruses. In replication deficient adenoviruses, parts of the virus genome are removed that include parts that are essential for at least one step of the virus infectious life cycle (herein also referred to as a missing replication function). Such recombinant viruses are therefore replication deficient, which means that said recombinant virus alone is incapable of completing the virus infectious life cycle. This type of recombinant adenovirus can, therefore, only replicate in a cell when the missing replication function encoded by said removed parts of the genome are somehow provided in said cell by other means. This is e.g. the case in so-called packaging cell lines wherein the function of the said removed parts are provided in the genome of the said cells, see e.g., WO 01/44280. Upon infection by a replication deficient virus, the said cells can complement for the missing replication function in trans, resulting in replication of the virus. Examples of replication deficient adenoviruses, sometimes also referred to as replication incompetent adenoviruses, are described in e.g. WO 95/12660, WO 98/46779, WO 98/46781, WO 00/71078, and U.S. Pat. No. 5,932,210.

Replication competent adenovirus is defined herein in that the virus comprises, as part of its genome, the function to be replicated in at least one type of target cell, wherein replication is solely dependent on the replication functions provided by the virus, in combination with the endogenous cellular machinery of the target cells.

The term "function to be replicated" includes the factors such as proteins, encoded by the virus, necessary for replication of the virus in the target cells (herein also referred to as viral replication factors). As indicated above, said factors may be endogenous for the said virus, but may also be functional analogues, encoded by the viral genome, e.g. in cases wherein the gene encoding the endogenous viral factor is deleted from the viral genome. It is important to note that these factors are encoded by the viral genome and are not to be complemented by exogenous factors encoded in target cells. Thus, viruses, of which the replication is dependent on one or more replication functions, being deleted from the virus, but introduced in the target cell, are defined to be replication deficient, and are therefore not part of the present invention. The invention as claimed relates to replication competent recombinant viruses, i.e. wherein the viral genes encoding viral replication factors, essential for regulation of virus replication in the target cells are present on the viral genome.

In a first type of replication competent recombinant adenovirus said parts that are essential for at least one step of the adenovirus infectious life cycle are also removed, but the essential functions of said parts are complemented by inserting functional expression cassettes for heterologous proteins that provide said essential functions in the recombinant adenovirus genome. This type of recombinant adenovirus is referred to herein as a heterologously trans-complemented adenovirus, and therefore is to be regarded as replication competent according to the definition presented herein.

A second type of replication competent recombinant adenovirus is the so-called conditionally replicating adenovirus (CRAd). In CRAds one or more parts of the adenovirus genome are removed, including parts that are essential for at least one step of the adenovirus infectious life cycle under certain physiological conditions (herein also "first conditions") but not under certain other physiological conditions (herein also "second conditions"). Said second and first conditions could, e.g., be dictated by the physiological conditions that exist in a particular type of cells (herein also "second cells"), but not in another type of cells (herein also "first cells"). Such a second type of cell is e.g. a cell derived from a particular type of tissue, where said cell contains a protein that is not or much less present in cells from other tissues (first type of cells). An example of a second type of cell is a cell that has lost proper cell growth control, such as e.g. a cancer cell, where said cell either lacks a protein that is present in cells that have not lost proper cell growth control or where said cell has gained expression (or over-expression) of a protein that is not or much less present in cells that have not lost proper cell growth control. Another example of said second conditions are the conditions that exist in a particular stage of the cell cycle or in a particular developmental stage of the cell, where a certain protein is expressed specifically. Thus CRAds can be designed such, that replication thereof is enabled in particular cells, such as cancer cells or a particular type of cancer cells, whereas in normal cells, replication of CRAds is not possible. This is known in the art, and reviewed e.g. by Heise and Kirn, J. Clin. Invest. 105(2000):847-851; Alemany et al., Nat. Biotech. 18(2000):723-727; Gomez-Navarro and Curiel, Lancet Oncol. 1(2000):148-158).

In a third type of replication competent recombinant adenovirus no parts of the adenovirus genome have been removed or said parts of the adenovirus genome that are removed do not include parts that are essential for at least one step of the adenovirus infectious life cycle. This type of replication competent has a capacity to replicate in cells like the parental unmodified adenovirus does and is therefore referred to as a true replication competent adenovirus. In general, the replication of recombinant adenoviruses is restricted to cells of a particular animal species or group of animal species. E.g., recombinant adenoviruses derived from human adenoviruses can only transverse a complete life cycle in human cells, with very inefficient replication occurring at high dose in cells of some other species.

The production of recombinant adenoviruses usually starts with genetic engineering of at least a part of the adenovirus genome by standard molecular biology techniques known in the art. In some cases, a full-length recombinant adenovirus construct comprising all elements required for replication in at least a certain type of cell is made, in other cases the recombinant adenovirus genome is separated over two or more constructs that share sequence homology. Next, the adenovirus genome (comprised by one or more constructs) is introduced into cells that allow replication of said recombinant adenovirus by DNA transfer methods known in the art, including but not restricted to calcium phosphate precipitation, DEAE-dextran mediated transfection, lipofectamine mediated transfection, electroporation, and the like. Procedures using an adenovirus genome that is separated over more than one construct rely on homologous recombination between the parts of the adenovirus genome that are shared by the constructs to occur in said cells to constitute a complete recombinant adenovirus genome.

After the recombinant adenovirus has started to replicate in cells into which the recombinant adenovirus genome has been introduced, said recombinant adenovirus can spread to other cells in the culture. The recombinant adenovirus can also be isolated from the culture medium or from lysates of the cells in which said recombinant adenovirus is replicating. The isolated recombinant adenovirus can then be used to re-infect new cells to further propagate and expand said recombinant adenovirus. In addition, said recombinant adenovirus can be administered to an animal or human body to infect cells in vivo. This administration can be done via several routes, including but not limited to direct injection into a tissue, oral administration, injection into the blood circulation, inhalation, injection into a body cavity, and application to the surface of a certain body area. Following infection of said cells in vivo, the recombinant adenovirus can replicate and spread to other cells in vivo, provided that the infected cells support replication of said recombinant adenovirus.

Replication deficient adenoviruses will not replicate in most cells in an animal body, except for special cell types that complement for the parts of the adenovirus genome that are removed and that are essential for the adenovirus infectious life cycle. Such special cell types include certain (growth factor-stimulated) cancer cells that exhibit what is generally referred to as "E1A-like activity" (Spergel and Chen-Kiang, Proc. Natl. Acad. Sci. USA 88(1991):6472-6476; Rancourt et al, Clin. Cancer Res. 5(1999):43-50; Steinwaerder et al, Hum. Gene Ther. 11(2000):1933-1948). Since the present invention requires that the genome of the recombinant adenovirus comprises function to replicate in and to have lytic capacity on target cells hampered in the p53-dependent apoptosis pathway replication deficient adenoviruses are not useful for the present invention. True replication competent adenoviruses will replicate in many different cells in an animal body, provided that they are derived from adenoviruses with the correct species tropism and that said cells express surface receptors for said adenoviruses. CRAds will only replicate in cells in which the particular conditions exist that are required for replication of the CRAd. CRAds are designed to meet the specific requirements for replication in a chosen (first) type of cell and not in other (second) types of cells. This property makes CRAds particularly useful for several embodiments of the present invention where the intend is to treat a disease by specific lytic replication of the recombinant adenovirus according to the invention in diseased cells in an animal or human body resulting in specific removal of said diseased cells from said body.

The adenovirus replication process constitutes the following steps: (1) binding of the adenovirus particle to the surface of the host cell via receptor molecules, (2) internalization of the virus particle by endocytosis, (3) escape from the endosome into the cytoplasm and transport towards the cell nucleus, during which the virus particle is partially broken down, (4) import of the adenovirus DNA genome into the cell nucleus, (5) expression of adenovirus proteins encoded by the early regions in the adenovirus genome, (6) replication of the adenovirus genome, (7) expression of adenovirus proteins encoded by the late regions in the adenovirus genome, (8) assembly of progeny adenovirus particles and inclusion of progeny adenovirus genomes into these particles, (9) induction of cell death, leading to (10) release of adenovirus progeny from the cell.

Important natural target cells for adenoviruses are non-dividing epithelial cells. These cells lack active machinery for the synthesis of DNA. Therefore, in order to replicate their DNA genome in these cells, adenoviruses induce the cellular DNA synthetic machinery. Adenovirus proteins encoded by the early region 1A (E1A) are potent inducers of DNA synthesis, cell growth and transformation, which they bring about through the formation of complexes with cellular proteins involved in cell cycle control. These effects of E1A cause cytotoxicity and induction of programmed cell death or apoptosis. In different cell lines, p53 dependent as well as p53 independent apoptosis has been documented after adenovirus infection (Teodoro and Branton, J. Virol. 71(1997):1739-1746; and references therein). Two proteins encoded by the early region 1B (E1B), E1B-19 kDa and E1B-55 kDa, and the early region 4 orf6 protein (E4orf6) suppress the cytotoxicity and apoptosis induced by E1A. The E1B-55 kDa and E4orf6 proteins cooperate to suppress apoptosis at least in part by forming a complex with p53 and inhibiting p53-mediated transactivation as well as promoting p53 degradation. The E1B-19 kDa protein interacts with proteins of the bcl-2 family to inhibit the caspase-9 dependent apoptosis pathway. The suppression of apoptosis prevents premature cell death, thereby allowing the adenovirus to complete its life cycle in the cell. In contrast, at late stages of infection cell death and lysis promote release of the virus progeny from the cell. An important mechanism used by adenovirus to accomplish this is through induction of apoptosis. Adenovirus proteins that were shown to be involved in late apoptosis induction or efficient cell lysis at late stages of infection by a currently unresolved mechanism include the E4orf4 protein (Shtrichman and Kleinberger, J. Virol. 72(1998):2975-2982; Marcellus et al, J. Virol. 72(1998):7144-7153) and the E3-11.6 kDa nuclear membrane glycoprotein, also termed adenovirus death protein (ADP) (Tollefson et al, J. Virol. 70(1996):2296-2306).

Cancer cells and cell lines are the result of neoplastic transformation. The genetic events underlying neoplastic transformation include activation of proto-oncogenes and inactivation of tumor-suppressor genes. A major player in this respect is the gene encoding the tumor-suppressor protein p53. The loss of normal function of p53 is associated with resistance to apoptosis, cell transformation in vitro and development of neoplasms in vivo. In fact, in approximately 50% of human cancers the gene encoding p53 is non-functional through deletion or mutation (Levine et al, Nature 351(1991): 453-456; Hollstein et al, Science 253(1991):49-53; Chang et al, J. Clin. Oncol. 13(1995):1009-1022). Also in cancer cells that do express wild-type p53 protein, apoptosis is hampered. At least in some cases and perhaps in all cases, this is the result of functional inactivation of p53 in these cells. E.g., loss of the tumor-suppressor protein p14ARF or overexpression of MDM2 protein can lead to functional inactivation of p53 by binding to the MDM2 protein and subsequent degradation (Landers et al., Oncogene 9(1994):2745-2750; Florenes et al., J. Natl. Cancer Inst. 86(1994):1297-1302; Blaydes et al., Oncogene 14(1997):1859-1868; Stott et al, EMBO J. 17(1998):5001-5014; Schmitt et al, Genes Dev. 19(1999): 2670-2677). Another example is functional inactivation of p53 as a result of the antagonizing binding of human papilloma virus (HPV) E6 protein in cervical carcinomas (Scheffner et al., Cell 63(1990):1129-1136) or of herpesvirus-8 latency-associated nuclear antigen in Kaposi's sarcoma (Friborg et al., Nature 402(1999):889-894). Thus, in many if not all cancers in vivo and cancer-derived or immortalized cell lines in vitro apoptosis is hampered as a result of one or more lesions in the p53-dependent pathway.

Loss of p53 function has also been documented in other diseases involving inappropriate cell survival, such as for example rheumatoid arthritis (Firestein et al., J. Clin. Invest. 96(1995):1631-1638; Firestein et al., Am. J. Pathol. 149 (1996):2143-2151; Firestein et al., Proc. Natl. Acad. Sci. USA 94(1997):10895-10900) and vascular smooth muscle cell hyperplasia (Speir et al., Science 265(1994):391-394; Kovacs et al., Am J. Pathol. 149(1996):1531-1539).

Interestingly, it has been observed that replicating adenoviruses kill cell lines that express functional p53 more rapidly than cell lines that are deficient in p53 (Hall et al, Nature Med. 4(1998):1068-1072; Goodrum and Ornelles, J. Virol. 72(1998):9479-9490; Dix et al, Cancer Res. 60(2000):2666-2672). The function of adenovirus-encoded proteins, in particular of the E1B-55 kDa protein, in relation to p53-dependent cell death remains unclear. On the one hand, wild type adenoviruses as well as recombinant adenoviruses lacking E1B-55 kDa were found to kill p53 wild type cancer cells more rapidly than p53 deficient cells, suggesting that the E1B-55 kDa protein does not play a role in the rapid cell death process (Hall et al, Nature Med. 4(1998):1068-1072; Dix et al, Cancer Res. 60(2000):2666-2672). On the other hand, adenoviruses expressing E1B-55 kDa or E1B-55 kDa mutants capable of forming a complex with p53 killed p53 wild type cells more rapidly than did adenoviruses expressing E1B-55 kDa mutants incapable of forming a complex with p53, suggesting that the E1B-55 kDa protein may play a role in the induction of cell death by adenovirus (Dix et al, Cancer Res. 60(2000):2666-2672).

The p53 protein is the central coordinator of damage-induced cell-cycle checkpoint control. In a perturbed cell, p53 can simultaneously induce growth arrest and apoptosis. p53 exerts these effects by functioning as a specific transcription factor that controls the expression of a large panel of genes involved in growth control, DNA repair, cell-cycle arrest, apoptosis promotion, redox regulation, nitric oxide production, and protein degradation (Polyak et al., Nature 389(1997):237-238; El-Deiry, Sem. Cancer. Biol. 8(1998): 345-357; Yu et al., Proc. Natl. Acad. Sci. USA 96(1999): 14517-14522; Hupp et al., Biochem. J. 352(2000):1-17; and references therein). The induction of apoptosis by p53 is mediated at least in part by activation of pro-apoptotic death genes of the bcl-2 family, such as bax, bak, and bcl-$x_s$ (Miyashita and Reed, Cell 80(1995):293-299; Han et al., Genes Dev. 10(1996):461-477). The immediate effector proteins of p53 as well as p53 itself target mitochondria, thereby releasing cytochrome c into the cytosol to activate the caspase cascade via the initiator caspase-9/Apaf-1 complex (Juergensmeier et al., Proc. Natl. Acad. Sci. USA 95(1998):4997-5002; Fearnhead et al., Proc. Natl. Acad. Sci. USA 95(1998): 13664-13669; Soengas et al., Science 284(1999):156-159; Marchenko et al., J. Biol. Chem. 275(2000):16202-16212).

There is evidence from mutation analysis that the transcription activation functions of p53 responsible for growth arrest and apoptosis can be dissected. For example, the p53 Q22/S23-mutant protein has abrogated growth arrest function but only attenuated apoptosis induction capacity (Venot et al., Oncogene 18(1999):2405-2410). On the other hand, several p53 amino acid 175 mutants were identified that retain cell cycle arrest function but are impaired in apoptosis induction (Ryan and Vousden, Mol. Cell. Biol. 18(1998):3692-3698). Furthermore, several p53 homologues have been identified, including p73 and p63, which share part of the functions with p53 (Kaghad et al., Cell 90(1997):809-819; Yang et al., Mol. Cell 2(1998):305-316). In the presence of the adenovirus E1B-19 kDa protein, which binds to and inactivates pro-apoptotic death genes of the bcl-2 family, the p53-dependent growth arrest pathway becomes apparent. Otherwise, apoptosis is dominant over growth arrest (Han et al., Genes Dev. 10(1996):461-477).

Recombinant adenoviruses, are finding increasing utility for the treatment of cancer and other diseases involving inappropriate cell survival. In particular, CRAds have been developed to selectively replicate in and kill cancer cells. Such cancer-specific CRAds represent a novel and very promising class of anticancer agents (reviewed by Heise and Kirn, supra, Alemany et al., supra; Gomez-Navarro and Curiel, supra). The tumor-selective replication of this type of CRAds is achieved through either of two alternative strategies. In the first strategy, the expression of an essential early adenovirus gene is controlled by a tumor-specific promoter (Rodriguez et al., Cancer Res. 57(1997):2559-2563; Hallenbeck et al., Hum. Gene Ther. 10(1999):1721-1733). The second strategy involves the introduction of mutations in viral genes to abrogate the interaction of the encoded proteins with cellular proteins, necessary to complete the viral life cycle in normal cells, but not in tumor cells (Bischoff et al., Science 274 (1996):373-376; Fueyo et al., Oncogene 19(2000):2-12; Heise et al., Clin. Cancer Res. 6(2000):4908-4914; Shen et al., J. Virol. 75(2001:4297-4307). During their replication in tumor cells CRAds destroy these cells by inducing lysis, a process that is further referred to as "oncolysis". The release of viral progeny from lysed tumor cells offers the potential to amplify CRAds in situ and to achieve lateral spread to neighboring cells in a solid tumor, thus expanding the oncolytic effect. The restriction of CRAd replication to tumor or hyperproliferative cells dictates the safety of the agent, by preventing lysis of normal tissue cells. Currently, CRAd-based cancer treatments are already being evaluated in clinical trials (e.g., Nemunaitis et al., Cancer Res. 60(2000):6359-6366; Khuri et al., Nature Med. 6(2000):879-885; Habib et al., Hum. Gene Ther. 12(2001):219-226).

However, despite very encouraging results from in vitro and animal studies, the anti-cancer efficacy of CRAds as a single agent in humans has been limited (Kirn et al., Nature Med. 4(1998):1341-1342; Ganly et al., Clin. Cancer Res. 6(2000):798-806; Nemunaitis et al., Cancer Res. 60(2000): 6359-6366; Mulvihill et al., Gene Therapy 8(2001):308-315). Thus, there is a clear need in the field of cancer treatment to increase the potency of recombinant adenoviruses as oncolytic agents. This could be achieved by enhancing their replication and lysis capacities.

Several approaches aimed at improving the replication and lysis capacities of recombinant adenoviruses, or at preventing loss of these functions from the wild-type adenovirus have been taken. It has been shown that it is better to retain the adenovirus E3 region in a recombinant adenovirus (Yu et al, Cancer Res. 60(2000):4200-4203) or, in case most of the E3 region is deleted, to at least retain the gene encoding the E3-11.6 kDa protein (Tollefson et al, J. Virol. 70(1996):2296-2306; Doronin et al, J. Virol. 74(2000):6147-6155). In addition, replication and cell lysis of recombinant adenoviruses have been improved by incorporation of cytotoxic genes (Zhang et al, Proc. Natl. Acad. Sci. USA 93(1996):4513-4518; Freytag et al, Hum. Gene Ther. 9(1998):1323-1333; Wildner et al, Gene Ther. 6(1999):57-62). It was also shown that recombinant adenoviruses are more potent in killing cancer cells when they contain the complete E1A region, but lack the E1B-19 kDa protein (Martin Duque et al, Cancer Gene Ther. 6(1999):554-563; Sauthoff et al, Hum. Gene Ther. 11(2000):379-388). Finally, the release of a recombinant adenovirus with deleted E1 and E3 regions from HeLa cervix cancer cells was enhanced by inducing apoptosis in these cells (Mi et al, Hum. Gene Ther. 12(2001):1343-1352). In the latter case, it was crucial that apoptosis was induced after progeny virus assembly in the cell had been completed. Premature apoptosis induction during viral DNA replication compromised virus production.

SUMMARY OF THE INVENTION

In many instances it is preferred that a recombinant adenovirus undergoes a rapid life cycle in a host cell. When a recombinant adenovirus is produced or when a recombinant adenovirus is used as a vector to produce a protein in cells, a rapid adenovirus life cycle speeds up the production process. When a recombinant adenovirus is used as a means to kill a population of cells, a rapid life cycle will add to the efficacy of the process. A rapid life cycle is of particular importance for the use of a recombinant adenovirus in vivo. Adenoviruses induce potent immune responses in the body of animals that inactivate said adenoviruses. This limits the duration of in vivo replication of an administered recombinant adenovirus. A faster life cycle will thus allow more cycles of progeny virus production within the time-span between administration and inactivation of the recombinant adenovirus. A situation where a rapid life cycle of a recombinant adenovirus is of particular importance in vivo is in the context of the treatment of a disease involving inappropriate cell survival. A paradigm example of such a disease is cancer. The anticancer potency of a recombinant adenovirus that is administered to a tumor in vivo depends on (1) the efficiency at which the virus disseminates throughout the tumor by producing progeny that can infect neighboring tumor cells, and (2) the efficiency at which the virus kills tumor cells via replication and lysis of the said cells. Thus, a rapid life cycle will result in a faster oncolysis, more cycles of new virus production per time, infection of more tumor cells in time, and, consequently, more effective tumor destruction.

Therefore, an important objective of the present invention is to provide recombinant adenoviruses that have a short replication time in a host cell. Said replication time is understood to mean the time between entry of the recombinant adenovirus into the cell and the release of progeny of said recombinant adenovirus from the cell.

It is a second objective of the present invention to provide recombinant adenoviruses that have a fast lytic capacity, i.e. meaning that the infected cells are lysed preferably within 7 days, more preferably within 4 days and most preferably within 2 days. A fast lytic capacity is understood to mean a short time required to lyse a host cell after entry of the recombinant adenovirus into said host cell.

In preferred embodiments of the invention, said host cell in which said recombinant adenoviruses have a short replication time and/or a fast lytic capacity is a cell with insufficient capacity to respond to a loss of cell-cycle checkpoint control, i.e. hampered in the p53 apoptosis pathway (herein also referred to as p53 dependent apoptosis pathway). Said cell is preferably a human cell. Non-limiting examples of host cells according to the invention are cancer or tumor cells, arthritic cells, hyperproliferative vascular smooth muscle cells and cells infected with a DNA virus other than said recombinant adenovirus.

In one variation of the invention, said host cell is a cell that is being cultured in vitro. In another variation of the invention, said host cell is a cell in an animal body, where it is preferred that said animal body is a human body.

In a preferred embodiment of the invention, said fast lytic capacity is the result of induction of cell death, wherein said cell death involves the p53-dependent apoptosis pathway.

The concept of the present invention is based on the following line of reasoning:
(1) To increase the rate of replication of a recombinant adenovirus in a cell at least one step of the replication process needs to be augmented.
(2) The step during the adenovirus life cycle that most critically determines the rate of virus replication is the step that requires the most time.
(3) For the type of adenovirus that is most widely used to generate recombinant adenoviruses, i.e., human adenovirus serotype 5, the steps 1-8 of the life cycle as described in the background of the invention are completed within approximately 2 days after cell entry. In contrast, the induction of lysis at late stages of infection occurs with various rates, depending on the host cell type, and may take as long as one week.
(4) Therefore, augmenting the lytic capacity of a recombinant adenovirus should have a major impact on the length of the recombinant adenovirus life cycle.
(5) The speed at which recombinant adenoviruses induce cell lysis appears related to the p53 status of the cell, where p53 deficiency correlates with delayed lysis.
(6) Many if not all hyperproliferative cells including cancer cells and immortalized cell lines carry one or more lesions in the p53-dependent apoptosis pathway.
(7) Hence, it should be possible to increase the speed at which recombinant adenoviruses induce cell lysis and complete their life cycle in a host cell by restoring a functional p53-dependent apoptosis pathway in the host cell during recombinant adenovirus replication.

The invention thus provides a replication competent recombinant virus, being capable to replicate and having lytic capacity in target cells, the said cells being hampered in the p53 dependent apoptosis pathway, the virus comprising in the genome thereof, the coding sequence of at least one restoring factor functional in restoring the p53 dependent apoptosis pathway in the said target cells, operably linked to one or more expression control sequences, functional in the said target cells.

Thus, the recombinant adenoviruses according to the invention are capable of replicating in a host cell and express a functional factor of the p53-dependent apoptosis pathway. The function of said factor is not, or insufficiently expressed by the target cells, and therefore, said factor is referred to as restoring factor. The restoring factor preferably comprises a protein. Non-limiting examples of said restoring factor are p53 protein, BAX protein, and family members thereof. As outlined above, it is to be clearly understood that the terms "replication competent" and "being capable to replicate in a host cell" mean that said recombinant adenoviruses alone are capable of completing their infectious life cycle in said host cell with the aid of the endogenous machinery of the said host cell, without a need to provide any functions encoded by any removed parts of the genome of said recombinant adenoviruses by other means, such as the provision thereof in the genome of the host cell. The said recombinant adenovirus is a replication competent adenovirus, preferably a conditionally replicating adenovirus or a heterologously trans-complemented adenovirus. Said recombinant adenoviruses are not replication deficient adenoviruses. It is furthermore preferred that said restoring factor is a mammalian protein, for example a human protein.

The term "restoring factor" means that said factor comprises at least one activity of the natural counterpart (i.e., the wild-type) of said factor, said activity being absent or insufficient in the target cell, where "activity" means at least in nature. It is also preferred that the activity at least equals that of the natural counterpart in amount, but is preferably even higher. Thus, "restoring factor" includes a wild-type factor and all its natural or synthetic derivatives that share at least one activity with said wild-type factor. The term "factor" comprises protein, the term protein being meant to include peptides or functional fragments of proteins or peptides.

The invention is furthermore based on the realization that it is important to retain the capacity of an adenovirus to counteract host cell apoptosis at least in part in order to prevent premature cell death before adenovirus replication is completed. Therefore, the recombinant adenoviruses of the invention should preferably retain one or more genes encoding proteins capable of regulating host cell apoptosis, in particular genes of the E1B and E4 region. Preferably, a gene encoding E1B-55 kDa protein or a functional analogue or derivative thereof is present on the genome of the recombinant adenoviruses of the invention, as will be shown in example 7 below. In this respect, the recombinant adenoviruses of the present invention are essentially different from those described in WO 00/29573 and WO 01/74403 that lack a functional E1B-55 kDa gene and do, therefore, not exhibit the useful characteristics of the recombinant adenoviruses of the present invention.

Most preferably, the full E1B region is present in the genome of the recombinant virus according to the invention, i.e. including coding sequences for the E1B-19 kDa protein. Furthermore, it is preferred that also the gene encoding E4orf6, or a functional analogue or derivative thereof, is present on the genome of the recombinant adenoviruses of the invention.

The invention also provides formulations comprising the recombinant adenoviruses according to the invention that can be used to preserve said recombinant adenoviruses and to administer said recombinant adenoviruses to cells. In one variation, the formulations are used to administer said recombinant adenoviruses to cells in vitro, in another variation the formulations are used to administer said recombinant adenoviruses to cells in vivo.

The invention furthermore provides methods to administer the formulations according to the invention to cells, leading to infection of said cells with the recombinant adenoviruses of the invention. In one variation, the methods are used to administer said formulations to cells in vitro, in another variation the methods are used to administer said formulations to cells in vivo.

The invention also provides compositions of the recombinant adenoviruses according to the invention and cells in which the recombinant adenoviruses according to the invention induce accelerated cell lysis and/or a faster release of virus progeny, compared to recombinant adenoviruses lacking coding sequences for the restoring factor according to the invention. In a preferred variation of the invention, said cells are cancer cells and said cell lysis is oncolysis. In a further preferred variation of the invention, said cells are human cells.

In another embodiment, the invention provides compositions of the recombinant adenoviruses according to the invention and tumors in which the recombinant adenoviruses according to the invention induce accelerated cell lysis and/or a faster release of virus progeny, compared to recombinant adenoviruses lacking coding sequence for the restoring factor according to the invention. In this aspect of the invention, it is preferred that said accelerated cell lysis and/or a faster release of virus progeny results in an accelerated lateral spread by said recombinant adenoviruses from infected cells to neighboring cells in said tumors, compared to recombinant adenoviruses lacking coding sequence for the restoring factor according to the invention. In this aspect of the invention, it is furthermore preferred that said accelerated cell lysis, faster release of virus progeny and/or accelerated lateral spread lead to a more effective destruction or growth inhibition of said tumors. In a preferred variation of the invention, said tumors are growing in an animal body. In a further variation, said animal body is a human body.

The invention furthermore provides methods to construct the recombinant adenoviruses according to the invention and to produce the formulations and compositions according to the invention.

The invention furthermore contemplates the use of the recombinant adenoviruses, methods and formulations according to the invention for the treatment of a disease which involves inappropriate cell survival, where it is preferred that said disease is a disease in a human being. In a particular embodiment of the invention said disease is cancer.

Hereinafter, in several embodiments of the invention a number of ways to provide said recombinant adenoviruses, formulations, methods, compositions, and uses are given. It is to be clearly understood that the description is not meant to in any way limit the scope of the invention as was explained in general terms above. Skilled artisans will be able to transfer the teachings of the present invention to other recombinant adenoviruses, restoring factors, formulations, methods, compositions, and uses that are not mentioned specifically herein without departing from the present invention.

It is also to be understood that the invention includes all combined uses of the recombinant adenoviruses, formulations, methods and compositions of the invention together with other methods and means to kill a population of cells, including but not limited to irradiation, introduction of genes encoding toxic proteins, such as for example toxins or pro-drug converting enzymes, and administration of chemical compounds, antibodies, receptor antagonists, and the like.

The definitions of the terms used in the invention specification and claims are deemed either to be sufficiently defined herein or otherwise being clearly understood in the art. Further, any nucleic acid or amino acid sequence of factors/proteins described herein are known sequences, wherein reference is made to commonly available sequence databanks, such as the databanks of EMBL, Heidelberg, Germany, and GenBank (NCBI), both herein incorporated by reference.

Hereinafter, the invention will be further exemplified by the following examples and figures. The examples show a number of ways to provide said recombinant adenoviruses, formulations, methods, compositions, and uses according to the invention. It is to be clearly understood that the examples are not meant to in any way limit the scope of the invention as was explained in general terms above. Skilled artisans will be able to transfer the teachings of the present invention to other recombinant adenoviruses, functional proteins, formulations, methods, compositions, and uses without departing from the present invention.

BRIEF DESCRIPTION OF THE DRAWINGS

FIG. 6. A conditionally replicating adenovirus expressing p53 kills human cancer cells more rapidly than the parental control virus not expressing p53. A549 (panel A), SaOs-2 (panel B) and U373MG (panel C) cells were infected with AdGFP (first row in each panel), Adp53 (second row in each panel), AdΔ24 (third row in each panel), or AdΔ24-p53 (fourth row in each panel), at an MOI dilution titration ranging from 100 pfu/cell to 0.01 pfu/cell as indicated above the panels. After 12 days, adherent cells were stained with crystal violet and scanned. Staining is a semi-quantitative measure for the amount of viable cells. Data shown are a representative example of three independent experiments performed.

DETAILED DESCRIPTION OF PREFERRED EMBODIMENTS

Figure 1:
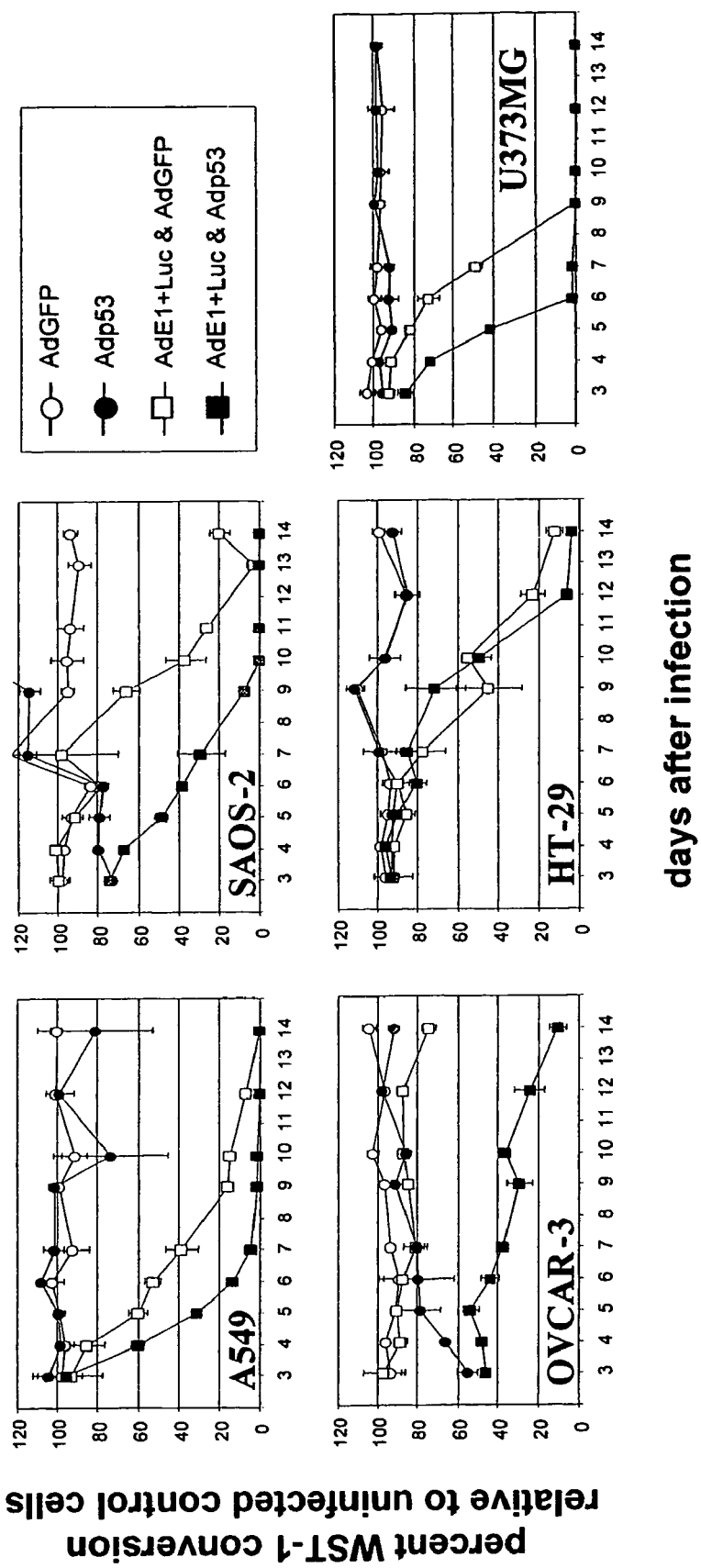
FIG. 1. Killing of human cancer cells by recombinant adenovirus replication is enhanced by p53 expression. Five human cancer cell lines (as indicated in the panels) with different p53 status were infected with AdGFP (open circles), Adp53 (closed circles), AdE1+Luc/AdGFP dual-virus mixture (open squares), or AdE1+Luc/Adp53 dual virus mixture (closed squares), and cultured up to 14 days. At various time-points, the cell viability was determined by WST-1 conversion assay and compared to the viability of uninfected control cultures. Data shown are the average percentages of viable cells +/−standard deviations of triplicate infections.

The invention and preferred embodiments appear from the appended claims. In one embodiment, the present invention provides a replication competent recombinant adenovirus capable of replicating in a host cell, said host cell being hampered in the p53 dependent pathway, i.e. having lost the capability to be induced to apoptosis through the p53 dependent pathway, and wherein the said virus comprises at least one open reading frame for a restoring factor, in particular a protein, capable of inducing p53-dependent apoptosis in the said target cells, said open reading frame being functionally linked to regulatory DNA sequences in such a manner that said factor is expressed in said host cell into which said recombinant adenovirus is introduced. In a variation of the present invention, a recombinant adenovirus is provided that comprises one or more open reading frames for a protein capable of inducing p53-dependent apoptosis functionally linked to regulatory DNA sequences in such a manner that said protein is expressed in a cell into which said recombinant adenovirus is introduced; in case of multiple open reading frames, at least two thereof each encode for a different protein capable of inducing p53-dependent apoptosis.

The virus can be replicated in the target cells in several ways as discussed above; the skilled person will be aware of suitable replication strategies useful for the practise of the invention.

The recombinant adenovirus according to the invention is a replication competent adenovirus, such as (1) a conditionally replicating adenovirus, or (2) a heterologously trans-complemented adenovirus, or (3) a two-component replication competent, heterologously trans-complemented, or conditionally replicating adenovirus consisting of as a first component a recombinant adenovirus that comprises at least one open reading frame for a protein capable of inducing p53-dependent apoptosis functionally linked to regulatory DNA sequences in such a manner that said protein is expressed in said host cell into which said recombinant adenovirus is introduced and as a second component a replication competent, heterologously trans-complemented, or conditionally replicating adenovirus, where a recombinant adenovirus according to possibilities 1 or 2 is preferred. Non-limiting examples of conditionally replicating adenoviruses according to the invention are derived from adenoviruses with controlled expression of at least one essential early adenovirus gene by a tumor-specific promoter, including but not limited to those described by Rodriguez et al. (Cancer Res. 57(1997):2559-2563) and by Hallenbeck et al. (Hum. Gene Ther. 10(1999):1721-1733), or adenoviruses with mutations in viral genes to abrogate the interaction of the encoded proteins with cellular proteins, necessary to complete the viral life cycle in normal cells, but not in tumor cells, including but not limited to those described by Heise et al. (Nature Med. 6(2000):1134-1139), Balague et al. (J. Virol. 75(2001): 7602-7611), Howe et al. (Mol. Ther. 2(2000):485-494) and Fueyo et al. (Oncogene 19(2000):2-12), or adenoviruses comprising both types of modifications. A non-limiting example of a heterologously trans-complemented adenovirus according to the invention is derived from a recombinant adenovirus with a functionally deleted E1 region that expresses the HPV E6 and E7 proteins (Steinwaerder et al., Mol. Ther. 4(2001):211-216).

For the purpose of the invention, the term "p53-dependent apoptosis" means cell death involving a pathway in which the p53 protein plays a role. Current knowledge on the regulation of programmed cell death and the position of p53 in the apoptotic pathways is reviewed in: Zoernig et al., Biochim. Biophys. Acta 1551(2001):F1-F37; Moll and Zaika, FEBS Letters 493(2001):65-69, included by reference herein. It is to be understood that said protein capable of inducing p53-dependent apoptosis includes the p53 protein itself, as well as its homologues, including but not limited to p63 and p73, and any other currently known or yet to be identified protein member of the p53-dependent apoptosis pathway, including but not limited to BAX, BAK, BOK/Mtd, BCL-$X_s$, Noxa/APR, PIDD, p53AIP1, PUMA, KILLER/DR5, Apaf-1 and the PIG products (Miyashita and Reed, Cell 80(1995):293-299; Kiefer et al., Nature 374(1995):736-739; Minn et al., J. Biol. Chem. 271(1996):6306-6312; Polyak et al., Nature 389 (1997):300-305; Wu et al, Nature Genet. 17(1997):141-143; Fearnhead et al., Proc. Natl. Acad. Sci. USA 95(1998):13664-13669; Juergensmeier et al., Proc. Natl. Acad. Sci. USA 95(1998):4997-5002; Soengas et al., Science 284(1999):156-159; Oda et al., Science 288(2000):1053-1058; Oda et al., Cell 102(2000):849-862; Pearson et al., Clin. Cancer Res. 6(2000):887-890; Lin and Benchimol, Nature Genet. 26(2000):122-127; Yu et al., Mol. Cell 7(2001):673-682). It is to be understood that it is not necessary that the expression of said protein capable of inducing p53-dependent apoptosis is regulated directly or indirectly by p53 transactivation. A protein that is capable of potentiating the p53-dependent apoptosis pathway by interacting with one or more members of said pathway is itself also regarded as a member of said pathway. Non-limiting examples of this type of protein capable of inducing p53-dependent apoptosis are BID and its truncated p15 form (tBID) that activate pro-apoptotic bcl-2 family members such as BAX and BAK (Desagher et al., J. Cell Biol. 144(1999):891-901; Wei et al., Genes Dev. 14(2000):2060-2071; Wei et al., Science 292(2001):727-730), and molecules such as BAD, HRK, Bik/Nbk, and Blk that induce apoptosis by antagonizing survival-promoting bcl-2 family members (Boyd et al., Oncogene 11(1995):1921-1928; Han et al., Mol. Cell. Biol. 16(1996): 5857-5864; Kelekar et al., Mol. Cell. Biol. 17(1997):7040-7046; Inohara et al., EMBO J. 16(1997):1686-1694; Hegde et al., J. Biol. Chem. 273(1998):7783-7786). Said protein also includes molecules capable of increasing the p53 amount in p53 wild-type cells or capable of trans-activating downstream effector proteins of p53. Non-limiting examples of proteins capable of increasing the p53 amount in p53 wild-type cells are the protein encoded by the melanoma differentiation associated gene-7 (mda-7) (Jiang et al., Oncogene 11(1995):2477-2486; Saeki et al., Gene Ther. 7(2000):2051-2057) and p14ARF in p14ARF-deficient cells. Although mda-7 has been described to mediate p53-independent apoptosis (WO 97/30732), it fulfils the definition of a member of the p53-dependent apoptosis pathway as defined herein, and is thus regarded as such for the purpose of the invention. Said protein capable of inducing p53-dependent apoptosis furthermore includes functional variants, analogues, or derivatives thereof such as mutant proteins and peptides that retain capacity to induce p53-dependent apoptosis. The terms "variant", "analogue" or "derivative" in relation to the above-described proteins or peptides include any substitution, variation, modification, replacement, deletion or addition of one (or more) amino acids from or to the coding sequence, provided that the variant, analogue or derivative retains similar function as compared with the original peptide or protein, i.e. the capacity to induce p53 dependent apoptosis. Such variants, analogues and derivatives are encompassed by the present invention.

A non-limiting example of a mutant protein that retains capacity to induce p53-dependent apoptosis is the p53 Q22/S23-mutant, which has abrogated growth arrest function but only attenuated apoptosis induction capacity (Venot et al., Oncogene 18(1999):2405-2410). Other non-limiting examples of mutant proteins that retain capacity to induce p53-dependent apoptosis are the p53 14/19, p53(d13-19) and CTS1 mutants (Lin et al., Genes & Dev. 8(1994):1235-1246; Kubbutat et al., Nature 387(1997):299-303; Bougeret et al., Cancer Gene Ther. 7(2000):789-798). The latter mutants lack the binding domain for the MDM2 protein and exhibit enhanced apoptotic activity in cancer cells expressing wild-type p53 (Bougeret et al., Cancer Gene Ther. 7(2000):789-798; Atencio et al., Mol. Ther. 4(2001):5-12; Lu et al., Cancer Res. 62(2002):1305-1310). It is to be understood that the term "MDM2 protein" is used as a general term to describe all homologues of this protein from different species, including but not limited to the human MDM2 protein that is sometimes referred to as "HDM2 protein". Yet another non-limiting example of a mutant protein that retains capacity to induce p53-dependent apoptosis is a fusion protein of p53 with a mitochondrial import leader peptide (Marchenko et al., J. Biol. Chem. 275(2000):16202-16212). A non-limiting example of a peptide that retains capacity to induce p53-dependent apoptosis is an amino acid fragment including the Bcl-2 Homology region-3 (BH3) of BAK (Chittenden et al., Nature 374(1995):733-736; Cosulich et al., Curr. Biol. 7(1997):913-920; Holinger et al., J. Biol. Chem. 274(1999):13298-13304). Another non-limiting example of a peptide that retains capacity to induce p53-dependent apoptosis is the truncated 18-kDa form of BAX with enhanced cell death activity (Wood and Newcomb, Exp. Cell Res. 256(2000):375-382; Gao and Dou, J. Cell. Biochem. 80(2000):53-72). It is preferred that said protein capable of inducing p53-dependent apoptosis is a mammalian protein, for example a human protein, or a functional variant, analogue or derivative thereof. It is furthermore preferred that said protein can interact with and be antagonized by at least one of the adenovirus E1B and/or E4 proteins. For example, if said protein is p53, or a functional variant, analogue or derivative thereof, it is preferred that said protein can interact with the adenovirus E1B-55 kDa and/or E4orf6 proteins. Amino acids in the p53 protein that are required for interaction with adenovirus E1B-55 kDa protein include Trp-23, Lys-24 and Pro-27 (Lin et al., Genes & Dev. 8(1994):1235-1246). Thus, if a functional variant, analogue or derivative of p53 is used in the invention, it is preferred that said functional variant, analogue or derivative contains p53 amino acids Trp-23, Lys-24 and Pro-27.

It is to be understood that "inducing p53-dependent apoptosis" includes active stimulation of the p53-dependent apoptosis pathway as well as restoration of the capacity of a cell to respond to a loss of cell-cycle checkpoint control by undergoing p53-dependent apoptosis. It is furthermore to be understood that "to interact with" as used herein includes physical complex formation between a protein or peptide with a counterpart protein or peptide as well as regulation by said protein or peptide of the activity of said counterpart protein or peptide without direct complex formation.

In one embodiment, the recombinant adenovirus according to the invention is characterized in that said protein capable of inducing p53-dependent apoptosis is the human p53 protein.

In a preferred embodiment, the recombinant adenovirus according to the invention is further characterized in that it comprises at least one of the genes of the E1B region, or a functional analogue or derivative thereof. In one variation of this embodiment, said recombinant adenovirus comprises the entire E1B region. In a second variation of this embodiment, said recombinant adenovirus comprises functional expression units for both the E1B-19 kDa and E1B-55 kDa proteins, or functional analogues or derivatives thereof. In a third variation of this embodiment, said recombinant adenovirus comprises a functional expression unit for the E1B-55 kDa protein, or a functional analogue or derivative thereof. It is to be understood that functional analogues of E1B-55 kDa include proteins from other viruses that are capable of interacting with p53, including but not limited to the HPV E6 protein and the herpesvirus-8 latency-associated nuclear antigen and functional derivatives thereof. It is further understood that functional analogues of E1B-19 kDa include anti-apoptotic members of the bcl-2 family of proteins and functional derivatives thereof. It is preferred that the proteins encoded by said genes of the E1B region or their functional analogues or derivatives are capable of interacting with the protein capable of inducing p53-dependent apoptosis according to the invention, or with a down-stream effector protein thereof.

In one variation, the recombinant adenovirus according to the invention is further characterized in that it comprises at least one of the genes of the E3 region. In one variation of this embodiment, said recombinant adenovirus comprises the entire E3 region. In a second variation of this embodiment, said recombinant adenovirus comprises functional expression units for one or more of the proteins encoded by the E3 region, such as for example E3-ADP.

In another variation, the recombinant adenovirus according to the invention is further characterized in that it lacks a functional E3 region. As is shown in the examples, the recombinant adenovirus according to the invention does not require an E3 region for efficient replication in and lysis of a host cell according to the invention. It is furthermore shown in example 9 that a conditionally replicating adenovirus according to this embodiment of the invention retains its conditional replication properties.

In another preferred embodiment, the recombinant adenovirus according to the invention is further characterized in that it comprises the gene encoding E4orf6, or a functional analogue or derivative thereof. It is preferred that the protein encoded by said E4orf6 gene, or a functional analogue or derivative thereof is capable of interacting with the protein capable of inducing p53-dependent apoptosis according to the invention, or with a down-stream effector protein thereof, or of interacting with a second protein encoded by said recombinant adenovirus that is capable of interacting with the protein capable of inducing p53-dependent apoptosis according to the invention, or with a down-stream effector protein thereof. A non-limiting example of said second protein is the adenovirus E1B-55 kDa protein or a functional variant, analogue or derivative thereof.

Control sequences operably linked to sequences, i.e. the open reading frame, encoding the protein or peptide of interest, include promoters/enhancers and other expression regulation signals. These control sequences may be selected to be compatible with the host cell for which the expression vector is designed. The term promoter is well-known in the art and encompasses nucleic acid regions ranging in size and complexity from minimal promoters to promoters including upstream elements and enhancers. The promoter is typically selected from promoters that are functional in mammalian cells, although promoters functional in other eukaryotic cells may be used. The promoter is typically derived from promoter sequences of viral or eukaryotic genes. For example, it may be a promoter derived from the genome of the type of cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase).

In one variation of the invention, said open reading frame for a protein capable of inducing p53-dependent apoptosis is functionally linked to regulatory DNA sequences in such a manner that said protein is constitutively expressed in a cell into which said recombinant adenovirus is introduced. In this case, the expression of said protein is driven by a constitutive or stable promoter. The present invention does not dictate the choice of said stable promoter. The type of promoter is chosen to accomplish a useful expression profile for said protein in the context of said recombinant adenovirus. Non-limiting examples of useful promoters for this variation of the invention include the Cytomegalovirus (CMV) immediate early promoter, The Simian Virus 40 (SV40) immediate early promoter, and promoters from eukaryotic household genes.

In another variation of the invention, said open reading frame encoding a protein capable of inducing p53-dependent apoptosis is functionally linked to one or more control sequences, i.e. regulatory DNA sequences, in such a manner that said protein is only expressed or is expressed at a higher level in a cell into which said recombinant adenovirus is introduced under certain conditions that can be modulated by an external signal, where the term "external" means having its origin outside of the DNA fragment encompassing said open reading frame and said regulatory DNA sequences. In this aspect of the invention, the expression of said protein is driven by a so-called regulatable or inducible promoter. Examples of said external signal include, but are not limited to, the addition or deprivation of a chemical compound, a shift in temperature, a decreased oxygen concentration, irradiation, and the like. Non-limiting examples of this kind of promoter include the heat shock protein 70 promoter, the promoter of an acute phase protein gene, such as the serum amyloid A3 gene or the complement factor 3 gene, the early growth response protein 1 promoter, the multidrug resistance gene 1 promoter, and promoters comprising one or more hypoxia-responsive elements, and fragments thereof (Kohno et al., Biochem. Biophys. Res. Comm. 165(1989):1415-1421; Varley et al., Proc. Natl. Acad. Sci. USA 92(1995):5346-5350; Hallahan et al., Nature Med. 1(1995):786-791; Dachs et al., Nature Med. 3(1997):515-520; Blackburn et al., Cancer Res. 58(1998):1358-1362; Binley et al., Gene Ther. 6(1999):1721-1727; Marples et al., Gene Ther. 7(2000):511-517). A special kind of regulatable promoter is a tissue- or cell type-specific promoter, where said external signal is provided by a protein that is only present in a particular type of cell or tissue. Non-limiting examples of tissue- or cell-type specific promoters are the prostate specific antigen promoter, the alpha-fetoprotein promoter, the albumin promoter, the carcinoembryonic antigen promoter, the cytokeratin 18 gene promoter, the kallikrein 2 promoter, the tyrosinase promoter, the osteocalcin promoter, the PAX-5 promoter and the alpha-lactalbumin promoter (Kaneko et al., Cancer Res. 55(1995):5283-5287; Richards et al., Hum. Gene Ther. 6(1995):881-893; Kozmik et al., Proc. Natl. Acad. Sci. USA 92(1995):5709-5713; Siders et al., Cancer Res. 56(1996):5638-5646; Chow et al., Proc. Natl. Acad. Sci. USA 94(1997):14695-14700; Shirakawa et al., Cancer Gene Ther. 5(1998):274-280; Gotoh et al., J. Urol. 160(1998):220-229; Anderson et al., Gene Ther. 6(1999):854-864; Yu et al., Cancer Res. 59(1999):4200-4203). Another special kind of regulatable promoter is a promoter that is responsive to an external signal that is provided by a protein that is not present in a particular type of cell or tissue. In particular, external signals that are absent in liver tissue are of interest in the context of in vivo administration of recombinant adenoviruses. Non-limiting examples of promoters that are responsive to external signals that are absent in liver tissue are the cyclooxygenase-2 promoter and the midkine promoter (Adachi et al., Cancer Res. 60(2000):4305-4310; Yamamoto et al., Mol. Ther. 3(2001):385-394). Another special kind of regulatable promoter is a promoter that is responsive to an external signal that is provided by a protein that is only present during a certain stage of the cell cycle. A non-limiting example of this kind of promoter is the promoter of a gene that is responsive to E2F, such as for example the adenovirus E2 gene or the E2F-1 gene. Another, not mutually excluding, special kind of regulatable promoter is a so-called transactivation response element (TRE). Said TRE is a first component of a transactivation system that comprises as a second component a transactivator protein, that is capable of binding with specificity to said TRE, thereby regulating the transcription of a gene linked to said TRE.

In yet another variation of the invention, said open reading frame for a protein capable of inducing p53-dependent apoptosis is functionally linked to regulatory DNA sequences in such a manner that said protein is only expressed in a cell into which said recombinant adenovirus is introduced during the late phase of adenovirus replication. Expression of said protein confined to the late phase of adenovirus replication is of particular interest in the context of a CRAd. Since said replication will only occur in cells in which certain conditions exist that are exploited by said CRAd to allow said replication, expression of said protein will also be confined to said cells in which said certain conditions exist. This variation of the invention will thus add to the specificity of said CRAd. In this aspect of the invention, it is preferred that expression of said protein is driven by the adenovirus major late promoter (MLP). In recombinant adenoviruses according to the invention where the MLP drives expression of said open reading frame it is preferred that the expression cassette for said open reading frame comprises the in cis acting sequences required to confer full transcriptional activity of the MLP during the late phase of adenovirus replication as defined by Mondesart et al. (Nucleic Acids Res. 19(1991):3221-3228), included by reference herein. A useful expression cassette for this aspect of the invention was disclosed in U.S. Pat. No. 5,518,913, included by reference herein. Alternatively, said open reading frame is functionally linked to the endogenous MLP.

The invention does not dictate the site of insertion of said open reading frame for a protein capable of inducing p53-dependent apoptosis functionally linked to regulatory DNA sequences in the genome of said recombinant adenovirus; said insertion may be at any location in said genome that does not inhibit replication of said recombinant adenovirus in said cell into which said recombinant adenovirus is introduced and where endogenous expression cassettes in said genome do not interfere with proper expression of said open reading frame. In non-limiting examples of the invention, said insertion is a replacement of the adenovirus E3-region or insertion between the E4 promoter and the right-hand ITR. DNA constructs to generate recombinant adenoviruses with insertions in the E3-region are known in the art, including but not limited to pBHG10 and pBHG11 (Bett et al., Proc. Natl. Acad. Sci. USA 91(1994):8802-8806), and insertions at other sites within the adenovirus genome can be made using standard molecular biology methods known in the art. In specific situations, it is preferred for proper expression of said open reading frame to shield said open reading frame for a protein capable of inducing p53-dependent apoptosis functionally linked to regulatory DNA sequences from other regulatory DNA sequences present in said adenovirus genome by flanking said open reading frame for a protein capable of inducing p53-dependent apoptosis functionally linked to regulatory DNA sequences by so-called insulator elements (Steinwaerder and Lieber, Gene Therapy 7(2000):556-567). In another variation of the invention, said open reading frame is inserted in place of an adenovirus gene, where it is preferred that said adenovirus gene is expressed during the late phase of adenovirus replication, and where it is further preferred that said adenovirus gene is functionally linked to the endogenous MLP.

In one embodiment of the invention, the recombinant adenovirus of the invention is characterized in that: (1) said open reading frame for a protein capable of inducing p53-dependent apoptosis is functionally linked to regulatory DNA sequences in such a manner that said protein is constitutively expressed in a cell into which said recombinant adenovirus is introduced, (2) said recombinant adenovirus comprises at least a gene encoding at least one of the proteins of the E1B region (or functional analogues or derivatives of the said proteins), but preferably an intact E1B region, and comprises preferably also at least a gene encoding at least one of the proteins of the E4 region (or functional analogues or derivatives thereof), but preferably an intact E4 region, and (3) said protein capable of inducing p53-dependent apoptosis or a direct or indirect down-stream effector protein of said protein capable of inducing p53-dependent apoptosis in the p53-dependent apoptosis pathway can interact with and be antagonized by at least one of the proteins of the E1B region and/or E4 region included in said recombinant adenovirus.

In another embodiment of the invention, the recombinant adenovirus of the invention is characterized in that: (1) said open reading frame for a protein capable of inducing p53-dependent apoptosis is functionally linked to regulatory DNA sequences in such a manner that said protein is constitutively expressed in a cell into which said recombinant adenovirus is introduced, (2) said recombinant adenovirus comprises at least coding sequences for the E1B-55 kDa and E4orf6 proteins, or functional analogues or derivatives thereof, and (3) said protein capable of inducing p53-dependent apoptosis or a direct or indirect down-stream effector protein of said protein capable of inducing p53-dependent apoptosis in the p53-dependent apoptosis pathway can interact with and be antagonized by at least one of the proteins of the E1B region and/or E4 region included in said recombinant adenovirus.

The recombinant adenoviruses of the invention are produced using molecular biology, virology and cell biology methods known in the art. A way to produce the recombinant adenoviruses according to the invention is described in detail in the examples section. It is to be understood, however, that this description is not meant in any way to limit the scope of the invention. Those skilled in the art will be able to derive the recombinant adenoviruses of the invention using other methods or by using variations of the methods described herein.

The invention also provides formulations comprising the recombinant adenoviruses according to the invention that can be used to preserve said recombinant adenoviruses and to administer said recombinant adenoviruses to cells. Said formulations preferably consist of said recombinant adenovirus and a diluent. Said diluent allows storage of said recombinant adenovirus for extended time and/or administration of said recombinant adenovirus to cells in culture and/or cells in an animal body, where it is preferred that said animal body is a human body. It is preferred that said diluent allows storage under lyophilized conditions. It is also preferred that said diluent allows both storage and administration of said recombinant adenovirus to cells in culture and/or cells in an animal body. It is to be understood that "to allow storage" means that during storage of said formulation the capability of said recombinant adenovirus to infect a cell is retained with a half-life higher than one week, where it is preferred that said half-life is more than one month, and where it is most preferred that said half-life is more than 6 months. Said storage may be at any temperature below 40° C., but it is preferred that said temperature is between 1° C. and 10° C., or that said temperature is below minus 60° C. It is to be understood that said administration to cells in culture and/or cells in an animal body means that said formulation and said cells are brought together resulting in introduction of said recombinant adenovirus into said cells. It is preferred that said diluent is not toxic to said cells and to said animal body. The invention does not dictate the exact composition of said diluent, but several useful diluents for the purpose of the invention are known in the art. Non-limiting examples of diluents useful in the invention include buffer solutions based on phosphate, such as PBS, or Tris or HEPES at a concentration between 10 and 25 mM and with a pH between 7.0 and 8.0, containing up to 150 mM NaCl or a combination of NaCl and KCl, and between 1 and 10 mM $MgCl_2$ or a combination of $MgCl_2$ and $CaCl_2$, with up to 3% sucrose or up to 40% glycerol. Other non-limiting examples of diluents according to the invention include the standard culture media for said cells known in the art, such as for example DMEM, IMDM or RPMI-1640, optionally supplemented with animal serum or serum components or recombinant serum proteins, chemically defined culture medium, including protein-free medium, and pharmaceutical diluents known in the art for administration of drugs into an animal body, such as for example Haemaccel (Behring Pharma). Optionally, said diluent may be further supplemented with additional constituents to increase physical stability of said recombinant adenovirus during storage or to increase said introduction into said cells. Said constituents may be different for each specific use of said formulation. Non-limiting examples of said additional constituents are polycations (Arcasoy et al., Gene Ther. 4(1997):32-38; Kaplan et al., Hum. Gene Ther. 9(1998):1469-1479; Lanuti et al., Gene Ther. 6(1999):1600-1610), polycationic polymers and cationic lipids (Fasbender et al., J. Biol. Chem. 272 (1997):6479-6489; Qiu et al., Hum. Gene Ther. 9(1998):507-520), polyamide compounds (Connor et al., Gene Ther. 8(2001):41-48), and the ingredients disclosed by Croyle et al (Mol. Ther. 4(2001):22-28). Optionally, said diluent may be further supplemented with additional constituents to improve the administration of said recombinant adenoviruses to said cells in an animal body. Non-limiting examples of such constituents are compounds that increase the permeability of cell layers in the wall of a blood vessel, such as for example bradykinin, serotonin and RMP-7 (Donahue et al., Gene Ther. 5(1998):630-634; Rainov et al., Hum. Gene Ther. 10(1999): 311-318), compounds that protect said recombinant adenoviruses from an immune response against said recombinant adenovirus, such as for example a protective liposome layer as described in WO 97/30732, or proteases that are active against extracellular matrix proteins (Kuriyama et al., Cancer Res. 61(2001):1805-1809), such as for example collagenases, gelatinases, matrilysin, stromelysines, dispase, trypsin, neuraminidase, serine proteases, and the like. If said cells in an animal body are cancer cells in a solid tumor, than it is preferred that said proteases are active against extracellular matrix proteins that are present in said tumor more abundantly than in other parts in said animal body, or that said protease is activated by proteins that are present more abundantly in said tumor than in other parts of said animal body. Non-limiting examples of such proteins that are present more abundantly in said tumor than in other parts of said animal body and that are capable of activating said proteases are membrane type metalloproteases (MT-MMPs) (Seiki, A.P.M.I.S. 107(1999):137-143). Part of the diluents and additional constituents described herein have been used in combination with recombinant adenoviruses other than the recombinant adenoviruses according to the invention, but not yet in combination with the recombinant adenoviruses according to the invention. Those skilled in the art will be able to define by proper investigation useful diluents to prepare a formulation according to the invention that results in the introduction of said recombinant adenovirus into cells for each particular use of the invention and each particular method of administration according to the invention.

The invention furthermore provides methods to administer the formulations according to the invention to cells, leading to introduction of the recombinant adenoviruses of the invention into said cells. In one variation, the methods are used to administer said formulations to cells in vitro, in another variation the methods are used to administer said formulations to cells in vivo. The methods according to the invention do not differ in any way from those known in the art to administer other recombinant adenoviruses to cells. In general, the recombinant adenoviruses of the invention are diluted to reach a useful concentration in a diluent according to the invention. In general, said diluent is isotonic to the conditions in an animal body, but in some cases it may be desired to use a diluent at a non-isotonic concentration. Said $MgCl_2$, $CaCl_2$, sucrose and glycerol are not required, and in the case of in vivo administration it is preferred that the concentration of glycerol is as low as possible. Said useful concentration of said recombinant adenovirus will be different for each different use of the invention. Skilled artisans will be able to determine said useful concentration by experimentation. Said formulation is brought into contact with said cells under either static conditions, such as in the case of administration to cells in culture or in the case of injection into an animal tissue, or under dynamic conditions, such as in the case of injection into the blood circulation of an animal body. Said formulation and said cells are brought into contact at a temperature between 0° C. and 40° C., where it is preferred that said temperature is between 30° C. and 40° C. In case said formulation is administered into an animal body, it is preferred that said formulation and said cells are brought into contact at the existing temperature in said animal body. In one variation of the invention, said administration is done at an ambient atmospheric pressure. In another variation of the invention, said administration is done at a pressure above atmospheric pressure. Said contact is maintained for a time period sufficiently long to allow introduction of said recombinant adenoviruses into said cells.

The invention also provides compositions of a recombinant adenovirus that comprises at least one open reading frame for a protein capable of inducing p53-dependent apoptosis according to the invention and cells in which said recombinant adenovirus replicates. Said recombinant adenoviruses have a host range that allows replication in said cells. Said composition results in at least one of the two following situations, i.e., (1) said cells are lysed more rapidly than when said cells are combined with a recombinant adenovirus other than the recombinant adenovirus according to the invention, and/or (2) virus progeny of said recombinant adenovirus according to the invention is released faster from said cell than virus progeny of a recombinant adenovirus other than the recombinant adenovirus according to the invention is released from said cell, where it is preferred that said composition results in both situations. In a preferred variation of the invention, said cells are cells that have lost capacity to respond to a loss of cell-cycle checkpoint control by undergoing p53-dependent apoptosis. In particular examples of this variation of the invention, said cells are rheumatoid arthritis cells or cancer cells. For the purpose of the invention, the terms "cancer cells" and "tumor cells" are defined as cells, having lost proper cell growth control, leading to uncontrolled growth and/or replication of the said cells in e.g. a mammalian body, or to accelerated growth/replication or immortality in vitro. Thus, the term includes malignant, pre-malignant and benign cancer cells. In a not mutually excluding preferred variation of the invention, said cells are human cells. In another not mutually excluding variation of the invention, said cells are cells in an animal body, where it is preferred that said animal body is a human body. The compositions of the invention are obtained by administering a formulation containing a recombinant adenovirus according to the invention to said cells by means of a method according to the invention.

In one embodiment of the invention, said cells that are part of a composition according to the invention, are cells in a solid tumor. In one variation of this embodiment, said tumor is maintained in culture in vitro. In this variation of the invention, said tumor may be artificially derived from cancer cells, such as for example a cell line-derived spheroid, or said tumor may be derived from an explant of a tumor in an animal body. In another variation of this embodiment, said tumor is present in an animal body. In this variation of the invention, said tumor may be surgically implanted into said animal body or said tumor may have arisen from said animal body. In the latter case, it is preferred that said animal body is a human body. In this embodiment of the invention, it is preferred that the more rapid cell lysis and/or faster release of virus progeny results in an accelerated lateral spread by said recombinant adenoviruses from infected cells to neighboring cells in said tumor, compared to recombinant adenoviruses lacking the protein capable of inducing p53-dependent apoptosis according to the invention. In this aspect of the invention, it is furthermore preferred that said more rapid cell lysis, faster release of virus progeny and/or accelerated lateral spread lead to a more effective destruction or growth inhibition of said tumor.

In another embodiment of the invention, said cells that are part of a composition according to the invention, are rheumatoid synovium cells. In one variation of this embodiment, said rheumatoid synovium cells are maintained in culture in vitro. In another variation of this embodiment, said rheumatoid synovium cells are present in an animal body, where it is preferred that said rheumatoid synovium cells are present in a chronically inflamed joint and where it is furthermore preferred that said animal body is a human body. In this embodiment of the invention, it is preferred that the more rapid cell lysis and/or faster release of virus progeny results in an accelerated lateral spread by said recombinant adenoviruses from infected cells to neighboring cells in said inflamed joint, compared to recombinant adenoviruses lacking the protein capable of inducing p53-dependent apoptosis according to the invention. In this aspect of the invention, it is furthermore preferred that said more rapid cell lysis, faster release of virus progeny and/or accelerated lateral spread lead to a more effective destruction or growth inhibition of said rheumatoid synovium cells.

In yet another embodiment of the invention, said cells that are part of a composition according to the invention, are vascular smooth muscle cells. In one variation of this embodiment, said vascular smooth muscle cells are maintained in culture in vitro. In another variation of this embodiment, said vascular smooth muscle cells are present in an animal body, where it is preferred that said vascular smooth muscle cells are present in an area of intimal hyperplasia, such as e.g. in atherosclerosis, restenosis or vascular graft occlusion, and where it is furthermore preferred that said animal body is a human body. In this embodiment of the invention, it is preferred that the more rapid cell lysis and/or faster release of virus progeny results in an accelerated lateral spread by said recombinant adenoviruses from infected cells to neighboring cells in said area of intimal hyperplasia, compared to recombinant adenoviruses lacking the protein capable of inducing p53-dependent apoptosis according to the invention. In this aspect of the invention, it is furthermore preferred that said more rapid cell lysis, faster release of virus progeny and/or accelerated lateral spread lead to a more effective destruction or growth inhibition of said vascular smooth muscle cells.

The invention furthermore contemplates the use of the recombinant adenoviruses, methods and formulations according to the invention for the treatment of a disease which involves inappropriate cell survival, where it is preferred that said disease is a disease in a human being. A treatment according to the invention will comprise administration of a recombinant adenovirus according to the invention, in a formulation according to the invention, to diseased cells in an animal body using a method according to the invention. In a particular embodiment of the invention said disease is cancer and said diseased cells are cancer cells, where it is preferred that said cancer cells are part of a solid tumor or a tumor metastasis. Depending on the type of disease and the nature of the diseased cells, a useful recombinant adenovirus, a useful formulation and a useful route of administration will be chosen. With respect to said recombinant adenovirus, a useful protein capable of inducing p53-dependent apoptosis may be chosen on the basis of prior investigation, but preferably also on the basis of knowledge of the genetic background of said disease in general, or more preferably of the genetic background of said diseased cells in particular. A useful formulation and route of administration will be chosen on the basis of knowledge on the localization of said diseased cells in said animal body, the characteristics of said diseased cells and the characteristics of other cells present in the part of said animal body to which said formulation is administered. Non-limiting examples of said route of administration include direct injection into a tissue containing diseased cells, oral administration, injection into the blood circulation, inhalation, injection into a body cavity, such as the pleural or peritoneal cavity, a joint, or a brain ventricle, injection into the lumen of a part of the gastro-intestinal or urogenital tract, and application to the surface of a certain body area, such as the skin or the otolaryngeal mucosa, for example by means of a mouth wash. If said route of administration is via injection into the blood circulation, it is preferred that said injection is done into an artery that leads to a part of said animal body that contains said diseased cells.

The invention furthermore contemplates that a treatment of a disease according to the invention is combined with other methods and means to kill a population of diseased cells known in the art, including but not limited to irradiation, introduction of genes encoding toxic proteins, such as for example diphteria toxin, or prodrug converting enzymes like thymidine kinase, cytosine deaminase or carboxylesterase, or cytokines like interleukin-2 or GM-CSF, or anti-angiogenic products like endostatin or angiostatin and administration of chemical compounds, antibodies, receptor antagonists, and the like. It is anticipated that such a combined treatment may result in a more effective killing of said population of diseased cells than either treatment alone. In addition, one treatment may potentiate the effect of the other treatment. For example, irradiation and certain chemical compounds are known to induce the p53-dependent apoptosis pathway. Thus, such treatments may potentiate the efficient cell lysis and virus progeny release of a recombinant adenovirus according to the invention.

EXAMPLES

Example 1

Production of Replication-Competent and Conditionally Replicating Adenoviruses Expressing the Human Tumor Suppressor Protein p53 and Control Adenoviruses without p53

To construct adenoviruses with an expression cassette for human p53 in place of the E3 region, the SVE-p53 expression cassette (SV40 early promoter-driven human p53 cDNA including intron-4) was released from pAdHumPwt.SVE (Ameyar et al., Oncogene 18(1999):5464-5472) by digestion with KpnI and XbaI (partial). The 2.6 kb fragment was inserted into KpnI/XbaI-digested pABS.4 (Microbix Biosystems, Toronto, Canada). The resulting construct was designated pABS.4-p53. pABS.4-p53 was digested with PacI and the 4 kb fragment carrying the SVE-p53 cassette and kanamycin resistance gene was inserted into PacI-digested pBHG11 (Microbix Biosystems). A clone with an insert in the orientation that places the SVE-p53 cassette on the adenovirus 1-strand was isolated and designated pBHG11-p53kan-L. The kanamycin resistance gene was removed by digestion with SwaI followed by self-ligation, yielding pBHG11-p53-L.

Replication competent adenoviruses were made by homologous recombination in 293 cells (Graham et al., J. Gen. Virol. 36 (1977):59-72) between pXC1 (Microbix Biosystems) or pXC1-derivatives with E1 mutations rendering the vectors conditionally replicating together with pBHG11 or pBHG11-p53-L. The pXC1-derivatives were pXC1-$\Delta$24, carrying a 24 by deletion in the pRb-binding CR2 domain in E1A (encoding amino acids LTCHEAGF (SEQ. ID NO: 5); Fueyo et al., Oncogene 19 (2000):2-12) and pXC1-$\Delta$ 55K carrying a deletion from the Sau3AI site at adenovirus serotype 5 (Ad5) nt 2426 to the BglII site at Ad5 nt 3328 encompassing a large part of the E1B-55 kDa protein open reading frame. This way, the following viruses were made: AdE1 with wild-type E1 region, Ad$\Delta$24 with the E1A CR2-mutation, Ad$\Delta$55K with the E1B-55 kDa protein-deletion, and the three p53-expressing derivatives AdE1-p53, Ad$\Delta$24-p53, and Ad$\Delta$55K-p53.

Viruses were plaque purified, propagated on A549 lung carcinoma cells (obtained from the ATCC, Manassis, Va.), and CsCl gradient purified according to standard techniques. The purified products were dialyzed extensively against 10 mM HEPES pH 7.4, 1 mM MgCl$_2$, 10% glycerol and stored at −80° C. until use. The E1 mutations and SVE-p53 insertion were confirmed by PCR on the final products. Expression of p53 protein was confirmed by infection of SaOs-2 p53-null cells (obtained from Dr. F. van Valen, Westfalische Wilhelms-Universität, Munster, Germany) followed by Western analysis with anti-p53 MoAb DO-7 (Dako, Glostrup, Denmark). Functional expression of p53 protein resulting in transactivation of p53-dependent promoters was confirmed by infection of SaOs-2 cells that were transfected with the p53-dependent reporter plasmid PG13-Luc (El-Deiry et al, Cell 75(1993) 817-825) and measurement of luciferase expression. Particle titers of all adenoviruses were determined by OD260 measurement and functional plaque forming unit (pfu) titers were determined by limiting dilution plaque titration on 293 cells according to standard techniques.

Example 2

Expression of Functional p53 Protein in Adenovirus-Infected Cells Enhances Cell Lysis To demonstrate that expression of a functional component of the p53-dependent apoptosis pathway during adenovirus replication augments lysis of the host cell, a dual-virus system was used in which cells were infected with equal amounts of the replication-competent adenovirus AdE1+Luc (a kind gift of Dr. R. Vogels, Crucell Holland B V, Leiden, The Netherlands) that was derived from wild-type Ad5 through replacement of the gp19k open reading frame in the E3 region by the firefly luciferase gene, and the replication-defective vector Adp53 (Ameyar et al., Oncogene 18(1999):5464-5472), expressing human wild-type p53 protein. This dual-virus system creates a situation where p53 is expressed in the context of a replicating adenovirus. As a negative control, Adp53 was replaced by the irrelevant control vector AdGFP (expressing CMV promoter-driven Enhanced Green Fluorescent Protein; van Beusechem et al., Gene Ther. 7(2000):1940-1946). In further control cultures, cells were infected with AdGFP or Adp53 only, to investigate the effect of apoptosis induction or growth arrest by p53 per se. A panel of human cancer cell lines with different p53 status was subjected to (dual) virus infection and cell viability was monitored over a two-week period. The cell lines included were: SaOs-2 osteosarcoma cells, that carry a homozygous p53 gene deletion (Masuda et al., Proc. Natl. Acad. Sci. USA 84(1987):7716-7719); HT-29 colon carcinoma and U373MG glioma cell lines, that carry a codon 273 R to H mutation in their p53 gene (Van Meir et al., Cancer Res. 54(1994):649-652; Rodrigues et al., Proc. Natl. Acad. Sci. USA 87(1990):7555-7559); OVCAR-3 ovary carcinoma cells, that carry a codon 248 R to Q mutation in their p53 gene (Yaginuma and Westphal, Cancer Res. 52(1992): 4196-4199); and A549 lung carcinoma cells, that express wild-type p53 protein (Lehman et al., Cancer Res. 51(1991): 4090-4096). SaOs-2 cells were obtained from Dr. F. van Valen, Westfalische Wilhelms-Universität, Munster, Germany; all other lines were purchased from the ATCC, Manassis, Va., USA. All cell lines were seeded 5·10$^4$ cells per well in 24-well plates in F12-DMEM/10% FCS and cultured overnight. The next day, dual-virus mixtures with equal pfu titers were prepared of AdE1+Luc with AdGFP or AdE1+Luc with Adp53 in F12-DMEM with 2% FCS. The mixtures were used to infect SaOs-2 cells at a multiplicity of infection (MOI) of 50 pfu/cell; A549 and U373MG cells at 100 pfu/cell; and OVCAR-3 and HT29 cells at 500 pfu/cell of each virus for 1 hour at 37° C. The cells were then washed once with 1 ml F12-DMEM/10% FCS and subsequently cultured in 0.5 ml F12-DMEM/10% FCS at 37° C. for up to 14 days. This procedure resulted in an efficient infection, as evidenced by detectable GFP expression in most of the cells infected with AdGFP two days after infection. Thus, many cells contained both viruses allowing the E1 proteins provided by AdE1+Luc to trans-complement Adp53 or AdGFP replication. At several time-points, cell viability was determined by removing the culture medium and replacing it by 200 µl 10% WST-1 reagent (Roche Diagnostics, Mannheim, Germany) in culture medium. Depending on the cell type and density, the formation of the formazan dye was allowed to proceed for 30-60 minutes at 37° C. One hundred µl WST-1 medium was transferred to a 96-well ELISA plate (Greiner, Frickenhausen, Germany) and the OD$_{450}$ was measured. WST-1 conversion was expressed as a percentage of the conversion by uninfected control cells, after subtraction of background values of WST-1 incubated in the absence of cells.

As can be seen in FIG. 1, AdE1+Luc/AdGFP-induced cell killing was severely delayed in p53-deficient SaOs-2, HT-29 and OVCAR-3 cell lines compared to p53 wild type A549 lung carcinoma cells. The p53-mutant U373MG cell line showed an intermediate rate of adenovirus-induced cell death. Adp53 infection alone affected p53-deficient SaOs-2 and OVCAR-3 cell lines to various degrees during the first few days after infection, but had no significant effect on the viability of p53 wild-type A549 cells and p53-mutant HT-29 or U373MG cells. Moreover, all Adp53-infected cultures fully recovered during the course of the experiment, showing that functional p53 expression alone does not result in an effective means to kill cancer cells. Importantly, AdE1+Luc/ Adp53-infected cells were killed much faster and more effectively than control AdE1+Luc/AdGFP-infected cells. Expression of functional p53 accelerated the killing of all cell lines except HT-29 by at least 3 days, irrespective of the cell line p53 status. Strikingly, OVCAR-3 cells actually required wild-type p53-expression to be sensitive to adenovirus-induced cell death at all. Hence, on most cancer cell lines tested, the combination of adenovirus replication and wild-type p53 expression caused the fastest and most effective cell death.

Example 3

Expression of Functional p53 Protein in Adenovirus-Infected Cells Accelerates the Release of Progeny Virus To demonstrate that the augmented cell lysis due to expression of a functional component of the p53-dependent apoptosis pathway during adenovirus replication results in an earlier release of virus progeny, the same dual-virus infection experiment was performed as described in example 2 and at various time-points during the 14-day culture period the AdE1+Luc virus titer was determined in the culture medium of dual-virus infected cells. To this end, the culture medium was harvested and cleared by centrifugation. The cell-free supernatant was serially diluted in F12-DMEM/10% FCS and used to infect A549 cells seeded 10$^4$ cells/well in 96-well plates 24 hours before infection. A control titration of AdE1+ Luc virus with known pfu titer was included. After 20-24 hours, the culture medium was replaced by Luciferase Chemiluminescent Assay System Reporter Lysis Buffer (Promega, Madison, Wis., USA) and the culture plates were subjected to a single freeze/thaw cycle. Chemiluminescence was measured with a Lumat LB 9507 luminometer (EG&G Berthold, Bad Wildbad, Germany) during the 10 seconds immediately after addition of the cell lysate to the Luciferase Assay Reagent. Values in the linear range of the serial dilution were used to calculate the luciferase infectious unit (IU) titer. This assay was linear over 3-4 orders of magnitude, with a threshold of approximately $10^3$ pfu.

Figure 2:
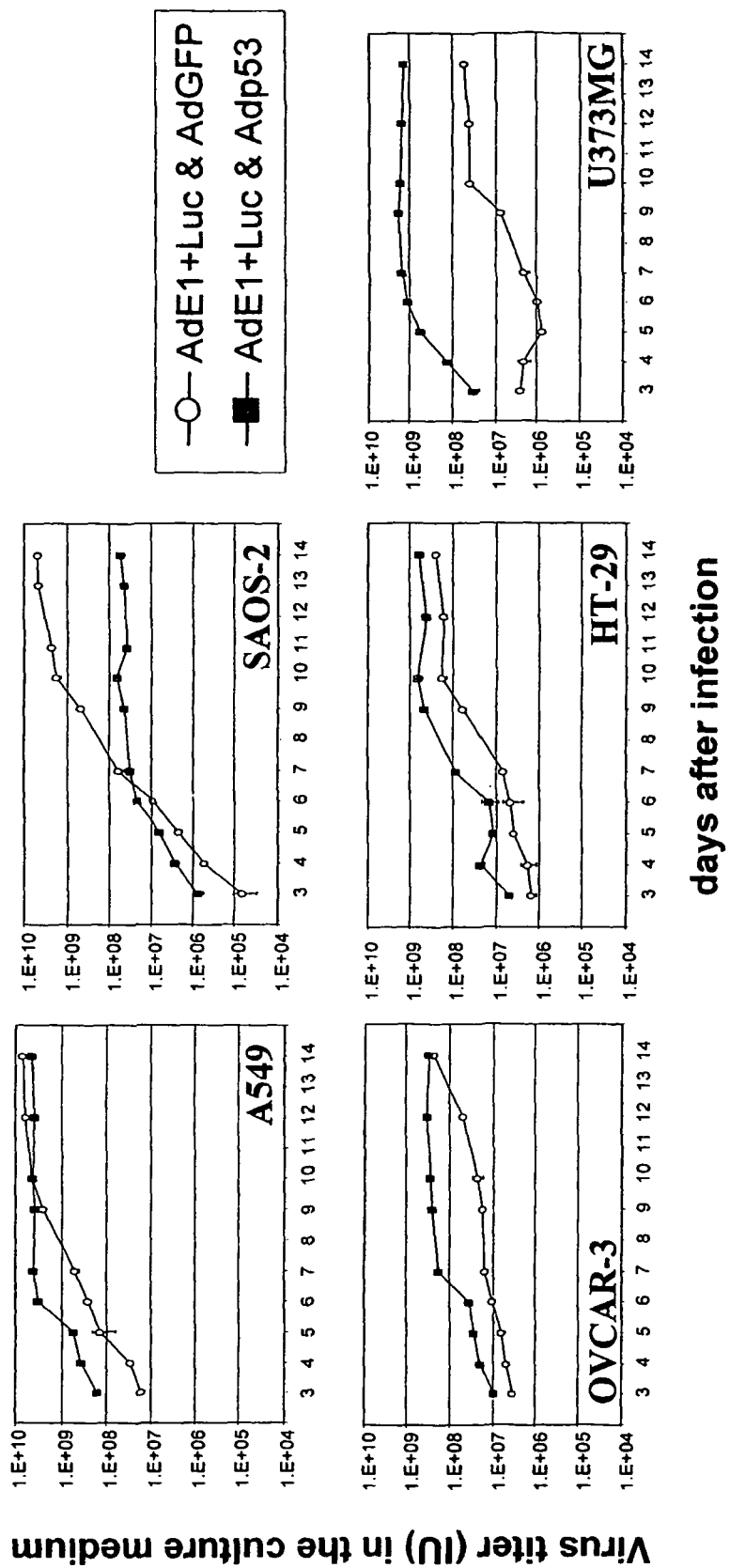
FIG. 2. Release of recombinant adenovirus progeny from infected human cancer cells is enhanced by p53 expression. Five human cancer cell lines (as indicated in the panels) with different p53 status were infected with AdE1+Luc/AdGFP dual-virus mixture (open circles), or AdE1+Luc/Adp53 dual virus mixture (closed squares), and cultured up to 14 days. At various time-points, the AdE1+Luc virus titer in the cell-free culture medium was determined on A549 cells. Data shown are the average virus titers +/−standard deviations of triplicate cultures.

FIG. 2 shows that the virus release rate of control AdE1+ Luc/AdGFP-infected cells correlated with the p53 status of the cell. Three days after infection, p53 wild-type A549 cells had already shed more than $10^7$ IU into the medium, while p53-null SaOs-2 cells showed 250-fold lower titers and mutant p53-expressing cells produced intermediate amounts. Introduction of functional p53 by means of AdE1+Luc/Adp53 infection enhanced the virus titers in the medium of all cell lines shortly after infection (with a range of 3-20-fold), irrespective of the cell line p53 status. In the case of SaOs-2 cells, where the p53-dependent lysis enhancement was most prominent, the acceleration of virus release was at the expense of a decrease in the total amount of virus produced over the 14-day period. The fast death of AdE1+Luc/Adp53-infected SaOs-2 cells lowered the total virus production approximately 100-fold in the experiment shown in FIG. 2 and approximately 20-fold in an independent second experiment. The virus production by the other cell lines was not negatively influenced by wild-type p53 introduction. In contrast, expression of functional p53 enhanced the total virus output in the medium of HT-29 and U373MG cells.

The faster accumulation of infectious virus particles in the culture medium could be the result of an accelerated virus production and/or an earlier virus release. To assess the cause for the observed titer differences early after infection, the AdE1+Luc virus titer was determined on cell lysates as well as on culture media of infected cells 3 days after infection. To this end, the culture medium was harvested and cleared by centrifugation. The cell-free supernatant was used to measure the titers of released AdE1+Luc virus. Non-adherent cells collected by centrifugation and adherent cells scraped from the culture plate were combined, resuspended in culture medium and subjected to three freeze/thaw cycles. The lysate was used to measure the AdE1+Luc virus titer inside the cells. The same method to determine the AdE1+Luc virus titer was used as described above. This experiment was performed on the same set of cell lines as above, and on two additional p53 wild type cancer cell lines, i.e., H460 large cell lung carcinoma cells (cultured in RPMI-1640/10% FCS) and MCF-7 breast carcinoma cells.

Figure 3:
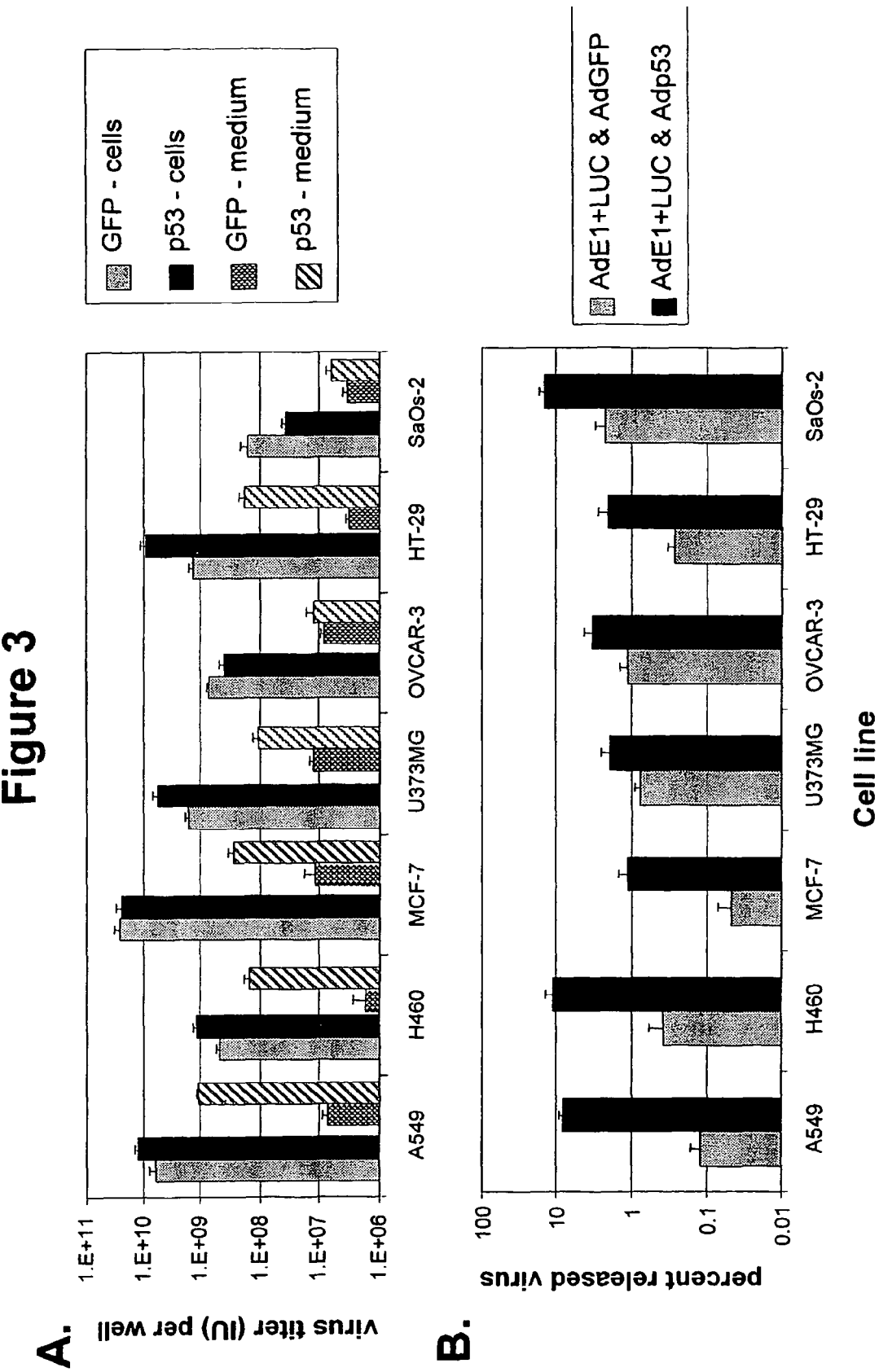
FIG. 3. Early release of recombinant adenovirus progeny from infected human cancer cells is augmented by p53 expression. Seven different human cancer cell lines were infected with AdE1+Luc/AdGFP dual-virus mixture, or AdE1+Luc/Adp53 dual virus mixture, and cultured for 3 days. After three days, the cell-free culture medium and the cells were harvested separately and the AdE1+Luc virus titer in these fractions was determined on A549 cells. Panel A shows the average virus titers+standard deviations of five infected cultures, determined on AdE1+Luc/AdGFP infected cells (gray bars), AdE1+Luc/Adp53 infected cells (black bars), the medium of AdE1+Luc/AdGFP infected cells (gray/black hatched bars), or the medium of AdE1+Luc/Adp53 infected cells (white/black hatched bars). Panel B gives the average percentages+standard deviations of virus released within 3 days, relative to the total amount of virus present inside cells and in the culture medium, calculated from the data in panel A, for AdE1+Luc/AdGFP infected cultures (gray bars) and AdE1+Luc/Adp53 infected cultures (black bars). Statistical significance of differences between treatment groups, i.e., virus titers and percentages of virus release in the presence versus in the absence of p53 expression, was tested by two-tailed Mann-Whitney test. Intracellular virus progeny production was not affected by p53 expression (p=0.80), In contrast, p53 expression increased the titer in the medium (p=0.007) and the proportion of virus progeny released within 3 days (p=0.004).

As can be seen in FIG. 3A, the amount of functional virus produced in infected cells within 3 days was not significantly affected by p53 expression (average 2.3-fold increased on different cell lines; range from a 4-fold decrease on SaOs-2 to a 7-fold increase on HT-29), while the titer in the medium was increased by p53 expression for all cell lines (average 45-fold increased; range from 1.6-fold on OVCAR-3 to 143-fold on A549). In AdE1+Luc/AdGFP-infected cultures, only 0.05-2.1% of the total virus progeny was released within three days (see FIG. 3B). Expression of p53 strongly augmented the virus release (average 20.4-fold; range 2.8-fold to 68-fold), resulting in 1.1-14.5% of the total virus already released within three days (see FIG. 3B). Hence, p53 expression during adenovirus replication reproducibly augmented the early release of virus progeny from the cell.

Example 4

The Lysis of Cancer Cells Infected with Replication-Competent Recombinant Adenoviruses or with Conditionally Replicating Recombinant Adenoviruses is Enhanced by Expression of Functional p53 Protein For the treatment of cancer, conditionally replicating adenoviruses (CRAds) are of particular interest. CRAds differ from replication-competent adenoviruses by specific mutations in their genome. An important type of CRAd is one that produces mutant E1A proteins incapable of binding to pRb (AdΔ24). To investigate if the invention is relevant in the context of AdΔ24, SaOs-2 cancer cells were infected with dual-virus mixtures consisting of the following components: (1) AdE1 (with wild type E1 region but deleted E3 region) or AdΔ24 (with a deletion in the pRb-binding CR2 domain in E1A and a deleted E3 region) at an MOI of 30, 10, or 1 pfu/cell, together with (2) AdGFP or Adp53 at an MOI of 30 pfu/cell. The MOIs were chosen such that most cells would be infected with component (2), and also with component (1) at the highest MOI used, but at lower MOI not all cells would initially be infected with component (1). In the latter case, more than one cycle of adenovirus replication is required to eradicate the entire cell population.

Figure 4:
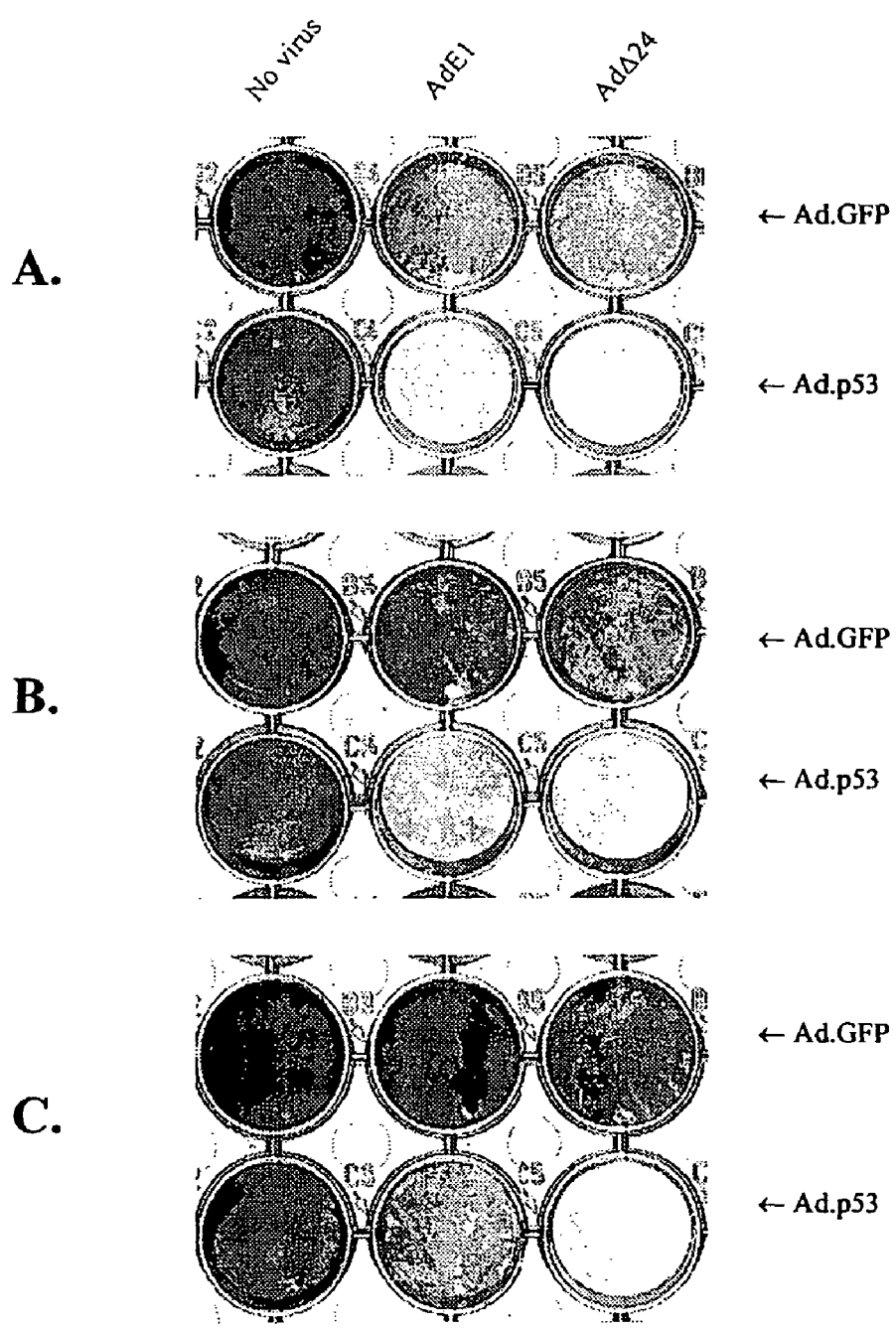
FIG. 4. Killing of SaOs-2 human osteosarcoma cells by conditionally replicating adenoviruses (CRAds) with mutant E1A and deleted E3 genes is enhanced by p53 expression. SaOs-2 cells were infected with AdGFP (upper row in each panel) or Adp53 (lower row in each panel) at MOI 30 pfu/cell, alone (first column in each panel) or together with AdE1 (second column in each panel), or AdΔ24 (third column in each panel) at MOI 30 pfu/cell (panel A), MOI 10 pfu/cell (panel B), or MOI 1 pfu/cell (panel C). After five days (panels A and B) or six days (panel C) culture, adherent cells were stained with crystal violet and scanned. Staining is a semi-quantitative measure for the amount of viable cells.

The same method to administer the viruses to the cells was used as described in example 2. Five or six days after infection, the culture medium was removed and the adherent cells were fixed for 10 minutes at room temperature with 4% formaldehyde in PBS and subsequently stained using 1% crystal violet dye in 70% ethanol for 20 minutes at room temperature. After several washes with water the culture plates were air-dried. The result of this experiment is shown in FIG. 4. The crystal violet dye stains all remaining cells on the surface of the culture dish. Thus, less staining indicates that more cells have been killed by the recombinant adenoviruses. From this experiment the following conclusions could be drawn: (1) both recombinant adenoviruses AdE1 and AdΔ24 were capable of killing SaOs-2 cells, (2) in the absence of p53 protein expression, neither of the two viruses was capable of completely eradicating the SaOs-2 cell monolayer during the span of the experiment, and (3) expression of functional p53 protein strongly enhanced the killing of SaOs-2 cells by both recombinant adenoviruses, showing that (4) expression of p53 increased the number of completed lytic replication cycles by AdE1 and AdΔ24 within the span of the experiment. These findings were confirmed in several independent experiments using dual-virus mixtures at various MOI on SaOs-2, A549 and U373MG cells. Ten to 100-fold enhanced oncolysis was observed when p53 was expressed. The enhancement was similar for AdE1 and AdΔ24. In conclusion, expression of a functional component of the p53-dependent apoptosis pathway enhances lysis of cancer cells by replication-competent recombinant adenoviruses as well as by conditionally replicating recombinant adenoviruses. Thus, the specific mutation that is introduced into the adenovirus genome to construct CRAd AdΔ24 does not interfere with the potentiation of oncolysis by a functional component of the p53-dependent apoptosis pathway. In addition, since both viruses lack a functional E3 region, the experiment showed that the adenovirus E3 region was not required for enhanced lysis of cancer cells by expression of a functional component of the p53-dependent apoptosis pathway. The accelerated cancer cell lysis and concomitant accelerated virus release, allowing faster virus spread through the cancer cell population, due to p53 expression resulted in a faster destruction of the entire cancer cell population. This further underlines the relevance of the invention for applications in the area of cancer treatment.

Example 5

Figure 5A:
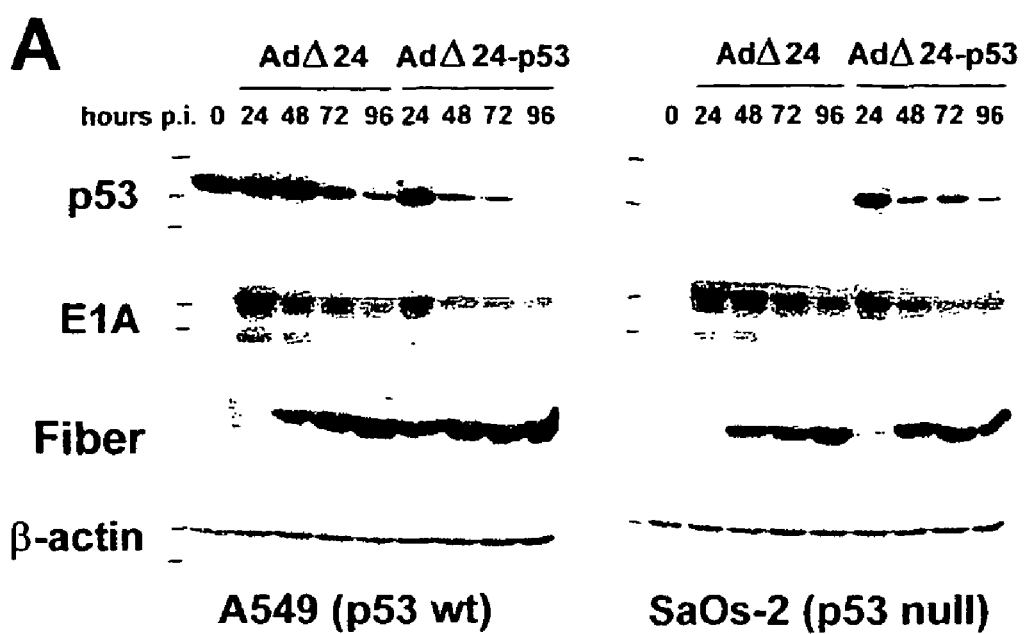
FIG. 5. Functional human p53 expression in human cancer cells infected with conditionally replicating adenoviruses expressing p53. A549 and SaOs-2 cells were infected with AdΔ24 or AdΔ24-p53 at 100 PFU/cell and cultured for up to 4 days. (A) Cell lysates were prepared and analyzed for E1A, fiber, and p53 expression by Western analysis. β-Actin analysis was included to control for equal loading. (B) Cells were transfected with PG13-Luc one day before infection with AdΔ24 (hatched bars), AdΔ24-p53 (black bars) or mock control (white bars). Two days post-infection, luciferase expression was measured in cell lysates. Data are mean relative light unit values+standard deviations of a representative experiment performed in triplicate.
Figure 5B:
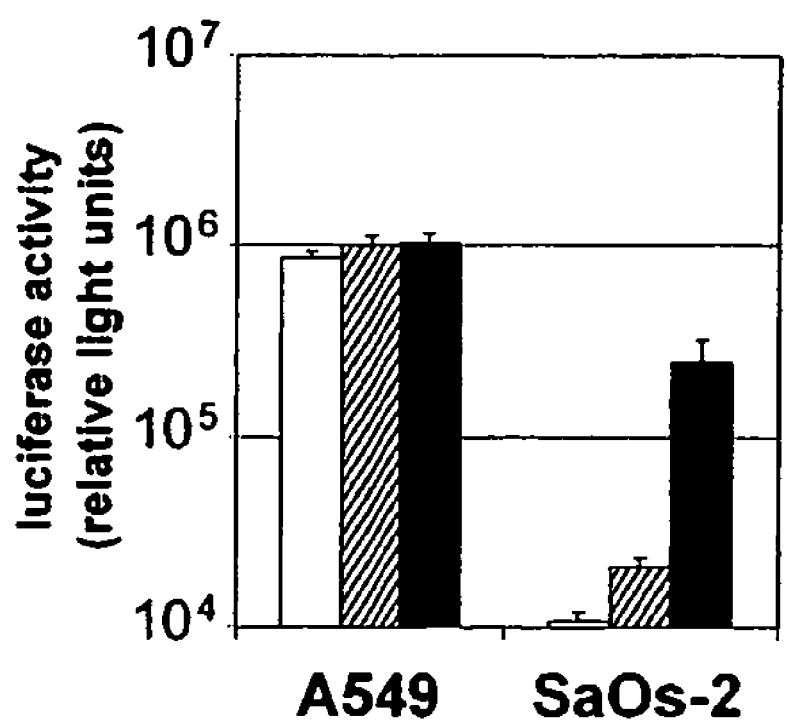

The Conditionally Replicating Adenovirus AdΔ24-p53 Expresses Functional p53 Protein During Replication in Cancer Cells The conditionally replicating adenovirus AdΔ24-p53 according to the invention was analyzed for functional p53 protein expression during replication in cancer cells by Western blot analysis (FIG. 5A) and p53-specific transactivation assay (FIG. 5B). For Western analysis, p53 null SaOs-2 and p53 wild type A549 cancer cells were seeded in 6-well plates at a density of 5·10$^5$ cells per well. The next day, the cells were infected with AdΔ24 or AdΔ24-p53 at 100 PFU/cell for 1 h, washed once in medium and incubated in fresh medium at 37° C. and 5% CO$_2$. After 24, 48, 72 and 96 hours incubation, the cells were harvested and lysed in 200 μl 140 mM NaCl, 0.2 M triethanolamine, 2 g/liter deoxychelate, 1 mM phenylmethanesulfonylfluoride, 50 μg/μl antipain by three freeze/thaw cycles. Lysates were cleared by centrifugation and protein concentrations were determined using the BCA Protein Assay Kit (Pierce, Rockford, Ill.). Equal amounts (15 μg) of protein were separated on a 10% SDS-PAGE gel and transferred to PVDF membrane (BioRad, Hercules, Calif.). Immunoblots were processed according to standard procedures, using primary antibodies for p53 (DO-7; DAKO, Glostrup, Denmark), E1A (SantaCruz Biotechnology, Santa Cruz, Calif.), fiber (4D2; Lab Vision, Fremont, Calif.), or β-actin (AC-15; Sigma, Saint Louis, Mo.), followed by anti-IgG-HRPO conjugate (DAKO) and Lumilight or Lumilight$^{PLUS}$ chemiluminescence detection reagent (Roche Diagnostics GmbH, Mannheim, Germany). As can be seen in FIG. 5A, adenovirus E1A and fiber proteins, indicative of early and late replication phases, were detected in AdΔ24-infected cells starting from 1 and 2 days post-infection, respectively. Endogenous p53 levels in A549 cells were suppressed due to AdΔ24 replication 3 days post-infection. As expected, no p53 was detected in p53-null SaOs-2 cells before and after infection with AdΔ24. In contrast, exogenous p53 was detected in SaOs-2 cells 1 day after infection with AdΔ24-p53. Thereafter, this p53 expression declined similarly as in CRAd-infected A549 cells. Hence, AdΔ24-p53 expressed p53 in p53-deficient cancer cells at regulated levels comparable to those found in CRAd-infected wild type p53 cells. Interestingly, AdΔ24-p53 appeared to replicate faster than AdΔ24 in both cell lines. In AdΔ24-p53 infected cells, fiber expression was detectable sooner and p53 expression declined more rapidly. Functional activity of the introduced p53 was confirmed by specific transactivation of the reporter plasmid PG13-Luc that contains a luciferase gene linked to a p53-dependent promoter (el-Deiry, et al., Cell 75(1993):817-825). Cells were seeded at 5·10$^4$ per well in 24-well plates and transfected with the p53-dependent reporter plasmid PG13-Luc using Lipofectamine PLUS (Life Technologies, Paisley, UK), according to the method described by the manufacturer. The next day, the cells were infected with AdΔ24 or AdΔ24-p53 for 1 h at 100 PFU/cell. Cells were cultured for 2 days and luciferase activity was measured as in example 3. P53-dependent transactivation was expressed as the luciferase activity in relative light units, after subtraction of the background expression in cells transfected with an irrelevant control plasmid. FIG. 5B shows that luciferase activity in PG13-Luc transfected SaOs-2 cells remained low after infection with AdΔ24, but rose markedly after infection with AdΔ24-p53, indicating that the expression of p53 caused transactivation of p53-dependent genes. Thus, while AdΔ24-p53 was replicating in p53 deficient or p53 wild type cancer cells, exogenous p53 was expressed in a regulated manner and this protein functionally transactivated down-stream effector genes of the p53-dependent apoptosis pathway.

Example 6

Conditionally Replicating Adenoviruses Expressing Functional p53 Show Enhanced Oncolytic Potency on Cancer Cells To investigate if the enhanced cell lysis and accelerated virus progeny release due to expression of functional p53 could also be accomplished if the p53 protein is expressed from a stable insert in the genome of a CRAd, the oncolytic potency of the p53-expressing CRAd AdΔ24-p53 was compared to that of the parental CRAd AdΔ24. A549, U373MG and SaOs-2 cells were seeded 5·10$^4$ cells per well in 24-well plates in F12-DMEM/10% FCS and cultured overnight. The next day, the cells were infected with AdGFP or Adp53 or AdΔ24 or AdΔ24-p53, diluted in F12-DMEM with 2% FCS to reach an MOI of 100 pfu/cell, 10 pfu/cell, 1 pfu/cell, 0.1 pfu/cell, or 0.01 pfu/cell, for 1 hour at 37° C. The virus-containing medium was then replaced by 1 ml F12-DMEM/10% FCS and cells were cultured at 37° C. After one week, 50% of the culture medium was refreshed. After 12 days, the culture medium was removed and the adherent cells were stained with crystal violet as described in example 4. As can be seen in FIG. 6, the control virus AdGFP had no effect on the viability of the cells. Adp53 virus only had a very modest inhibitory effect on SaOs-2 cells at the highest MOI. AdΔ24 exhibited a dose-dependent lytic activity on all three cell lines. Most importantly, AdΔ24-p53 killed all three cancer cell lines more effectively than did AdΔ24. An approximately 100, more than 100, or 10-fold lower titer of AdΔ24-p53 than of AdΔ24 was required to accomplish similar killing potency on A549, U373MG and SaOs-2 cancer cells, respectively. Hence, expression of a functional component of the p53-dependent apoptosis pathway from a stable insert in the genome of a conditionally replicating recombinant adenovirus enhanced the oncolytic potency of said recombinant adenovirus 10-100-fold. The oncolytic potency was enhanced irrespective of the cancer cell p53 genetic background.

In independent experiments, a larger panel of human cancer cell lines was subjected to the same analysis for oncolytic potency of AdΔ24-p53 versus AdΔ24. Expression of p53 from a stable insert in the AdΔ24 genome resulted in enhanced oncolytic potency on A431 epithelial carcinoma cells; U87MG, U251MG, U118MG and U373MG brain cancer cells; MDA-MB-231 and MCF-7 breast carcinoma cells; HeLa cervix carcinoma cells; A549 and H460 lung carcinoma cells; OVCAR-3 and SKOV-3 ovary carcinoma cells; 11B and 22A head and neck squamous carcinoma cells; PC-3 prostate carcinoma cells; T24 bladder cancer cells; HepG2 liver cancer cells; SaOs-2 osteosarcoma cells; NJB, CHP212, SH-SY5Y and SK-NAS neuroblastoma cells; SW1398, Colo205 and HT-29 colon carcinoma cells; and HM02 and MKN28 gastric carcinoma cells. Of a total of 32 human cancer cell lines subjected to this analysis so far, 27 (i.e., 84%) exhibited enhanced AdΔ24-induced lysis due to p53 expression. Thus, the invention has broad application for a variety of cancer types.

Example 7

Comparison of the Oncolytic Potency of AdΔ24-p53 and AdΔ55K-p53

Figure 7:
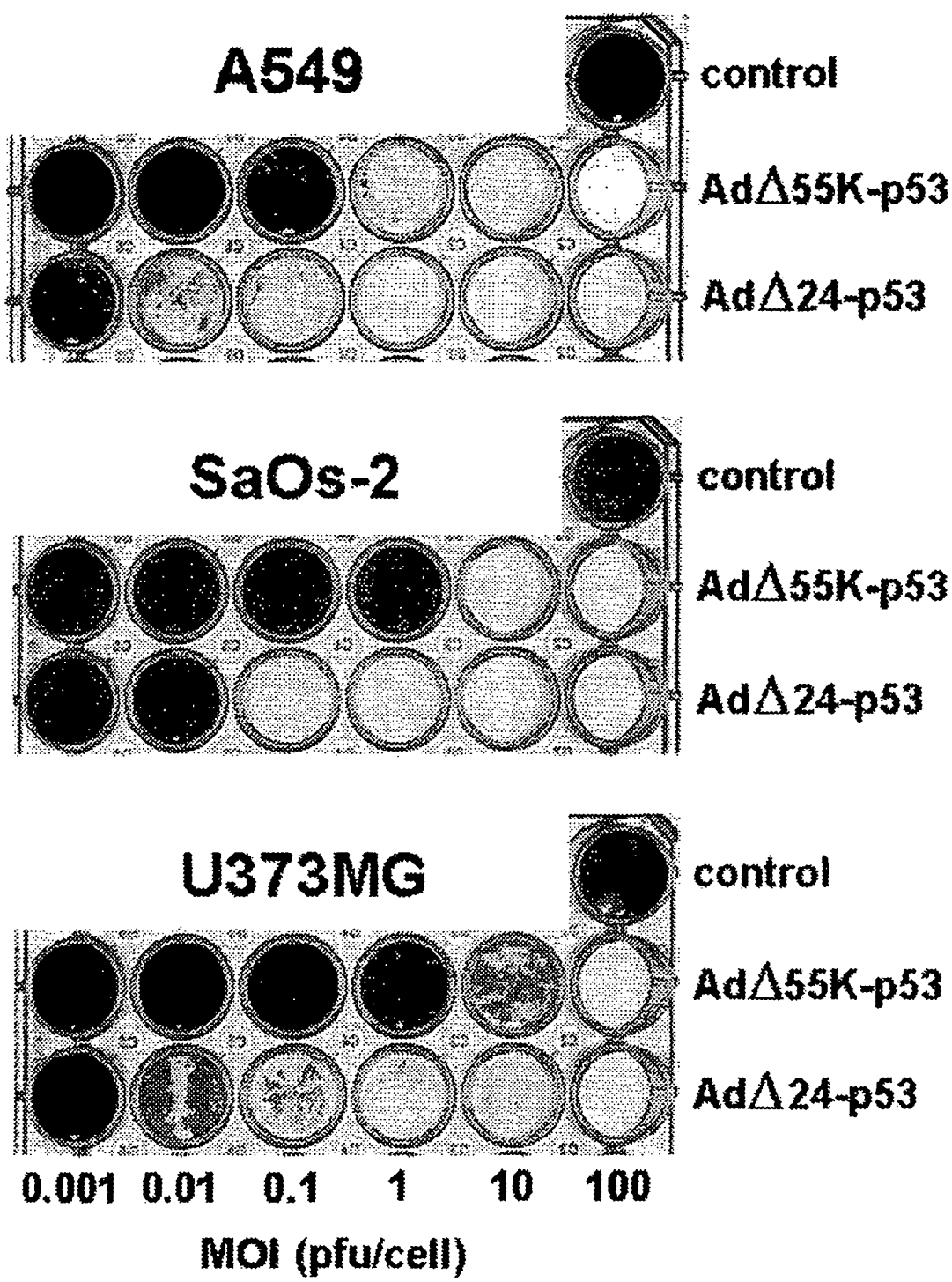
FIG. 7. A conditionally replicating adenovirus expressing both p53 and E1B-55 kDa protein kills human cancer cells more rapidly than a conditionally replicating adenovirus expressing p53 but not E1B-55 kDa protein. A549, SaOs-2 and U373MG cells (as indicated above the respective panels) were infected with AdΔ55K-p53 or AdΔ24-p53 as indicated, at an MOI dilution titration ranging from 100 pfu/cell to 0.001 pfu/cell as indicated below the panels. After 14 days, adherent cells were stained with crystal violet.

To investigate the role of the E1B-55 kDa protein in recombinant adenoviruses according to the invention, we compared the oncolytic potency of AdΔ24-p53 (with intact E1B-55 kDa gene) to AdΔ55K-p53 (with deleted E1B-55 kDa gene) using the same method as described in example 6. We included 3 human cancer cell lines with differing p53 status that had shown different susceptibilities to enhanced oncolysis due to p53 expression, i.e., p53 null SaOs-2 cells (approximately 10-times enhanced oncolysis), p53 wild type A549 cells (100-times enhanced oncolysis), and p53 mutant U373MG cells (more than 100-times enhanced oncolysis). FIG. 7 shows the result of crystal violet staining performed on day 14 after infection. As can be seen, AdΔ24-p53 was much more potent (approximately 100-times) on all three cell lines then AdΔ55K-p53. Thus, all or most gain in oncolytic potency by inclusion of the p53 gene into the genome of AdΔ24 was lost by deleting the E1B-55 kDa gene. Therefore, it is highly preferred that recombinant adenoviruses according to the invention comprise a functional E1B-55 kDa gene. AdΔ55K-p53 was designed as described in WO 00/29573 and WO 01/74403. This example therefore demonstrates that the recombinant adenoviruses of the present invention provide a much more effective destruction of a population of cancer cells than the recombinant adenovirus according to WO 00/29573 and WO 01/74403.

Example 8

Figure 8:
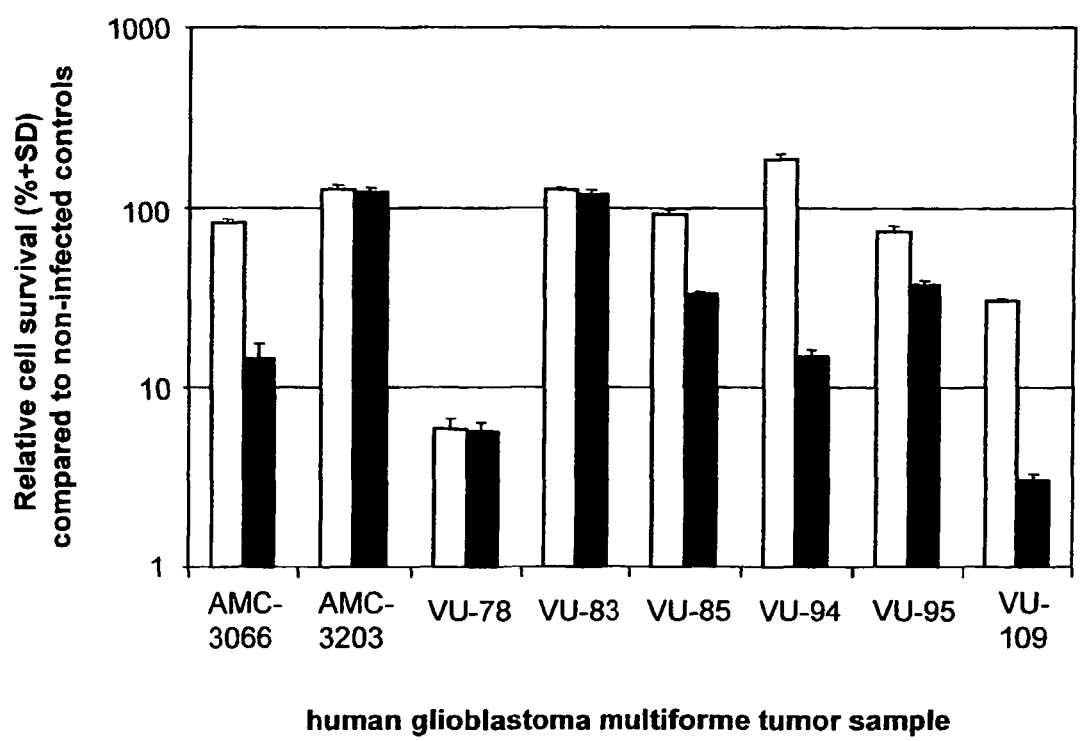
FIG. 8. A conditionally replicating adenovirus expressing p53 kills GBM cells from human patients with brain cancer more effectively than the parental control virus not expressing p53. Short-term cultured GBM cells from 8 different patients were infected with AdΔ24 (white bars) or AdΔ24-p53 (black bars) at 1 pfu/cell and cultured for 12-25 days. Cell survival was measured by WST-1 conversion assay. Data shown are mean cell survival percentages compared to non-infected control cultures+standard deviation of triplicate measurements.

AdΔ24-p53 Exhibits Enhanced Anti-Cancer Efficacy Against Primary Brain Tumor Specimens from Human Patients It is an objective of the invention to use the recombinant adenoviruses of the invention for the treatment of cancer in humans. To assess the utility of the recombinant adenoviruses of the invention for this purpose, we evaluated the oncolytic potency of the recombinant adenoviruses according to the invention on short-term cultured tumor specimens from eight patients with brain cancer. Fresh tumor material was collected during brain tumor surgery after informed consent and processed within 3 hours after dissection. Pathologic confirmation of the diagnosis was made on the tumor material that was processed for cell culture. All samples included in the study were characterized as glioblastoma multiforme (GBM). Primary GBM cells were obtained after mechanical dissociation of tumor resection material and cultured in DMEM supplemented with 10% FCS and antibiotics. CRAd replication experiments were done before passage 10. Depending on cell size, short-term GBM cell cultures were seeded 2 to $5 \cdot 10^5$ cells per well to prepare sub-confluent monolayers in 6-well plates. The next day, the cells were infected at 1 pfu/cell with AdΔ24 or AdΔ24-p53 for 1 hour at 37° C., or cultured in medium as a negative control. Subsequently, the virus was replaced by culture medium and the cells were cultured at 37° C. for 12-25 days until cytopathogenic effects became apparent, at which time they were analyzed for cell survival by WST-1 conversion assay. All cells (adherent and non-adherent) were harvested and reseeded in triplicate dilution titrations in a 96-well culture plate and cultured in 10% WST-1 (Roche Diagnostics, Mannheim, Germany) in culture medium for up to 16 hours before $OD_{450}$ measurement. Values in the linear range were used to calculate the relative survival compared to non-infected control cells, after subtraction of the background. The results obtained on the panel of GBM cultures are shown in FIG. 8. As can be seen, AdΔ24 killed only one specimen (VU-78) effectively, while all other specimens were more or less resistant to this virus. AdΔ24-p53 was more effective than AdΔ24 on 5 of these resistant specimens. Two specimens (AMC3203 and VU-83) were resistant to both viruses. We could establish that this was due to lack of adenovirus receptor expression on the surface of these cells (not shown). Thus, AdΔ24 CRAd exhibited oncolytic potency on one of eight GBM specimens whereas AdΔ24-p53 killed six of eight samples. These findings show that the recombinant adenoviruses according to the invention have increased oncolytic potency against diseased cells from humans suffering from a disease involving inappropriate cell survival.

Example 9

Figure 9:
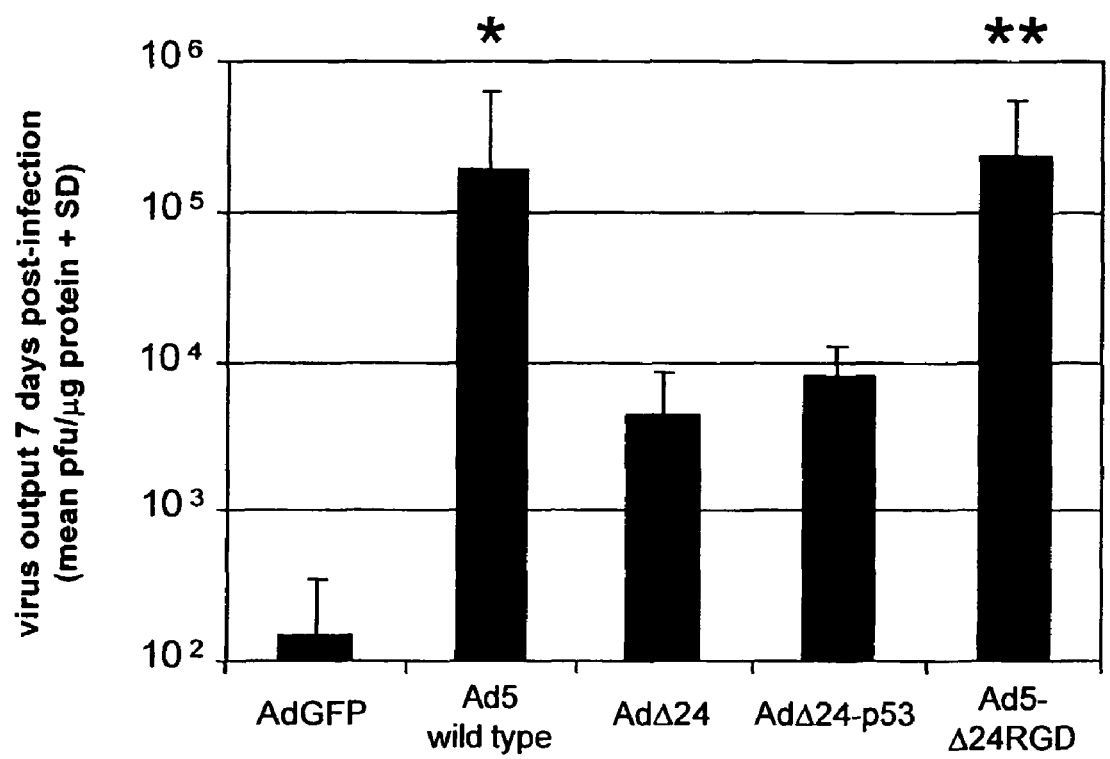
FIG. 9. A conditionally replicating adenovirus expressing p53 exhibits attenuated replication property on normal human brain tissue in vitro. Human brain tissue pieces were infected with the indicated recombinant adenoviruses and cultured for 7 days. After culture, the viable virus titer contained within the tissue pieces was determined by limiting dilution titration. Data shown are mean pfu titers per microgram protein+standard deviation of 5 (AdGFP) or 6 (all other viruses) infected brain tissue pieces. Statistical significance of differences between treatment groups was tested by Kruskal-Wallis test with Dunn's multiple comparison. *, p<0.05 compared to AdGFP; **, p<0.001 compared to AdGFP. All other differences were not significant.

Expression of Functional p53 from the Genome of a Conditionally Replicating Adenovirus does not Affect the Conditional Replication Properties of the Recombinant Adenovirus Conditionally replicating adenoviruses should exhibit attenuated replication properties on non-malignant tissues. To evaluate this for the recombinant adenoviruses according to the invention, we examined the replication of AdΔ24-p53 on normal human brain tissue and compared this to the replication on this tissue by the parental control CRAd AdΔ24, by wild type Ad5 (positive control replication competent adenovirus), by AdGFP (negative control replication deficient adenovirus), and by Ad5-Δ24RGD (Suzuki et al., Clin. Cancer Res. 7(2001):120-126; a CRAd with the Δ24-mutation in the CR2-domain of E1A, an RGD-motif insertion in the fiber gene and an intact E3 region). A piece of normal brain tissue was removed from the corticotomy tract during surgery of a patient with meningioma and cut into small pieces of a few mm, using 23 Gauge needles. The pieces were washed twice in culture medium and individually subjected to $10^8$ pfu adenovirus (AdGFP: 5 pieces; all other adenoviruses: 6 pieces) in 100 microliter culture medium for 1.5 hours. Subsequently, they were washed in 1 ml culture medium and cultured in 200 microliter culture medium for 7 days at 37° C. Two days after infection, successful infection was confirmed by detecting green fluorescence in AdGFP transduced tissue pieces. On day 7, all pieces were washed in 1 ml PBS and frozen at −80° C. in 250 microliter PBS. The pieces were lysed by three freeze/thaw cycles at 37° C. and in liquid nitrogen, following which the lysates were cleared by centrifugation. The protein content of the lysates was determined using the BCA Protein Assay Kit (Pierce, Rockford, Ill.). The titer of infectious adenovirus in each lysate was determined by limiting dilution titration on 293 cells in triplicate using standard procedures. Differences between output titers of different adenoviruses were tested by Kruskal-Wallis test with Dunn's multiple comparison. FIG. 9 shows the adenovirus titers 7 days post-infection in the tissue pieces, normalized per microgram protein. As can be seen, human brain tissue that had been infected with replication deficient control virus AdGFP contained a low titer of adenovirus, indicative of some residual input AdGFP still present after 7 days. Tissue pieces that were infected with replication competent control virus Ad5 contained much more virus (more than 1000-fold higher titer; p<0.05), showing that wild type adenovirus replication during 7 days cultivation yielded infectious adenovirus progeny. CRAd AdΔ24 exhibited an approximately 40-fold lower output titer than Ad5, confirming that its replication is attenuated on normal tissue. The titer of AdΔ24-p53 adenovirus according to the invention was not significantly different from that of AdΔ24 (only 1.7-times higher; p>0.05). Moreover, the virus output of AdΔ24 or AdΔ24-p53 infected brain tissue was also not significantly different from that of AdGFP infected pieces (p>0.05). Hence, the attenuated replication due to the A24-mutation was retained in the adenovirus according to the invention. In contrast, Ad5-Δ24RGD replicated as good in normal brain tissue as did the wild type Ad5 control adenovirus and produced significantly more virus than the AdGFP input control (p<0.001). Ad5-Δ24RGD did thus not exhibit a conditional replication property. Possibly, this was due to the expression of adenovirus E3-encoded protein in Ad5-Δ24RGD infected cells. If so, this would indicate that the modification to the CRAd genome according to the invention is preferred over other strategies aimed at enhancing the lytic capacity of a CRAd, such as expressing the adenovirus E3-11.6 kDa gene.

Example 10

Figure 10:
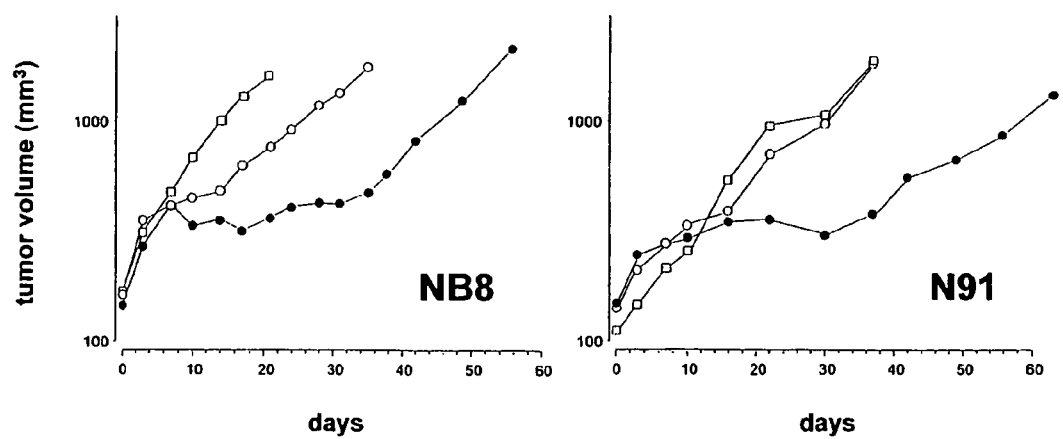
FIG. 10. A conditionally replicating adenovirus expressing p53 has enhanced anti-tumor efficacy on human tumors growing in the body of nude mice compared to the parental control virus not expressing p53. Two different human neuroblastoma tumors from patients, i.e., NB8 (left panel) and N91 (right panel) were established as subcutaneous tumor lines in nude mice. Mice carrying tumor nodules of 100-200 mm$^3$ (8 or 9 mice in each treatment group) received intratumoral injections of PBS (open squares) as negative control, AdΔ24 (open circles), or AdΔ24-p53 (closed circles). Tumor volumes were measured regularly. Data shown are mean tumor volumes of treatment groups from the first day of injection until the day at which the first mouse of the treatment group had to be sacrificed because its tumor size exceeded 2000 mm³.

AdΔ24-p53 Exhibits Enhanced Anti-Cancer Efficacy Against Human Neuroblastoma Tumor Xenografts Growing in Nude Mice To evaluate the anti-cancer potency of the recombinant adenoviruses according to the invention in an animal body in vivo, AdΔ24 and AdΔ24-p53 were injected for 5 subsequent days at $10^8$ pfu per injection into human neuroblastoma tumors growing as xenografts on the flanks of nude mice. As negative control, mice received injections with PBS. Subsequently, tumor sizes were measured regularly using calipers and volumes were calculated using the formula: volume $(mm^3)$=(length (mm)×width$^2$ $(mm^2)$)/2. Tumor growth speed (i.e., time required to reach 5× the tumor volume at the start of the experiment) was calculated for each individual animal. Differences between tumor growth speeds of different treatment groups were tested by Kruskal-Wallis test with Dunn's multiple comparison. As can be seen in FIG. 10, AdΔ24 injections caused a small, but not significant (p>0.05), tumor growth delay compared to PBS injected controls in NB8 tumors and had no effect at all in N91 tumors. In contrast, AdΔ24-p53 caused a significant tumor growth delay in both human neuroblastoma xenografts (NB8: mean 29 days, p<0.01; N91: mean 38 days, p<0.001). These findings show that the recombinant adenoviruses according to the invention have increased growth inhibitory potency against human solid tumors growing in an animal body.

Example 11

Figure 11:
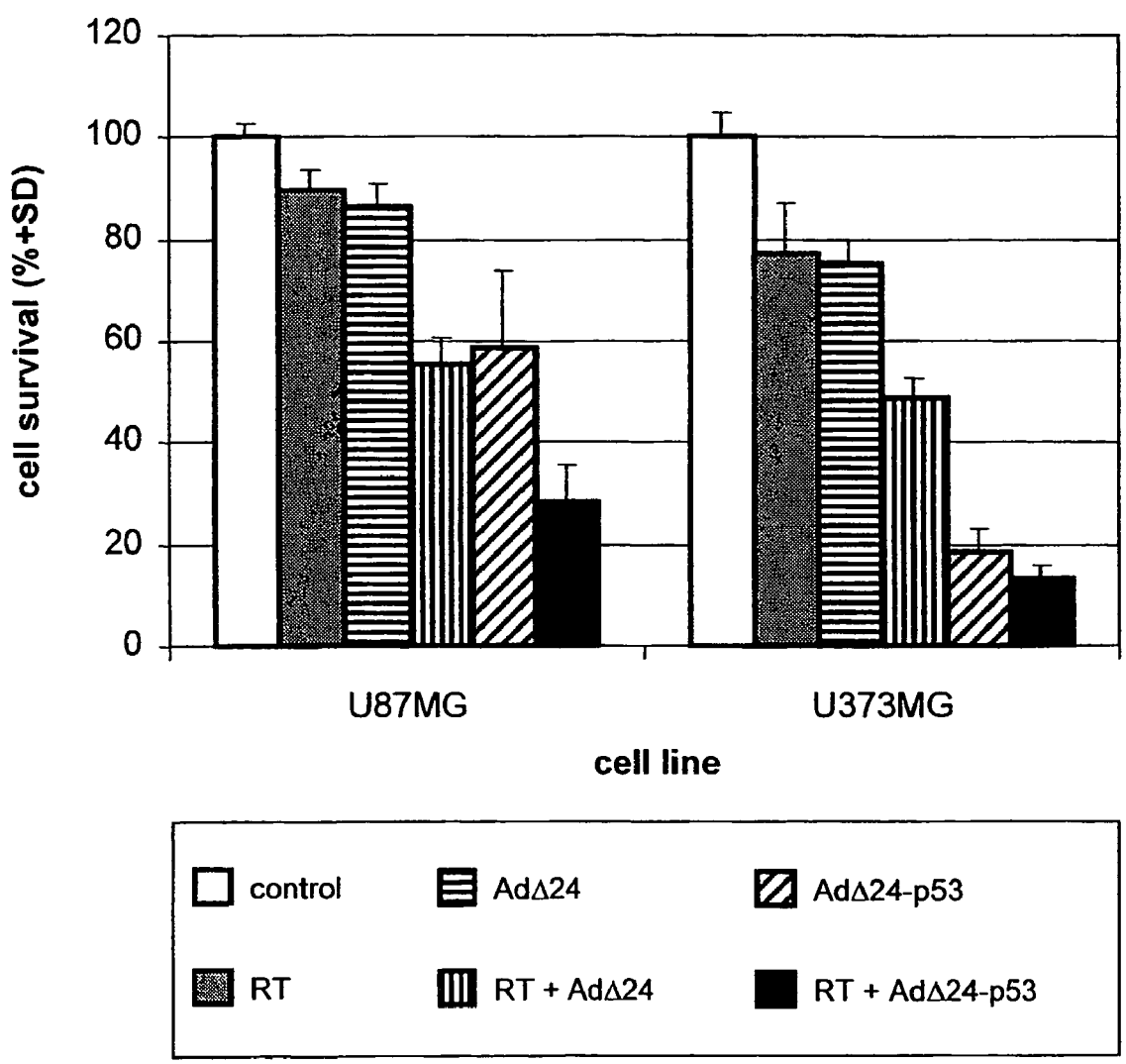
FIG. 11. Anti-cancer efficacy of combined treatment with conditionally replicating adenovirus expressing p53 and irradiation. U87MG (p53 wild type) and U373MG (p53 mutant) glioma cells were subjected to 4 Gy radiation therapy (RT), 0.5 pfu/cell AdΔ24 or AdΔ24-p53 virus therapy, or RT followed by virus therapy, as indicated. Eight days post-infection, relative cell survival was determined by WST-1 conversion assay. Data shown are mean percent cell survival+ standard deviation compared to non-infected non-irradiated control cultures.

The Combination of AdΔ24-p53 Together with Irradiation Exhibits More Effective Anti-Cancer Efficacy Against Human Glioma Cells then Either Treatment Alone, or the Combination of AdΔ24 Together with Irradiation Elimination of cancer cells with CRAds has been shown more effective when the treatment is combined with chemotherapeutic agents or irradiation (e.g., Heise et al., Nature Med. 3(1997):639-645; Yu et al., Cancer Res. 61(2001):517-525; Rogulski et al., Cancer Res. 60(2000):1193-1196; Chen et al., Cancer Res. 61(2001):5453-5460). Therefore, we investigated if combination treatment with irradiation and the recombinant adenoviruses according to the invention would also be more effective than either treatment alone. U87MG (wild type p53) and U373MG (mutant p53) human brain cancer cells, seeded 5·10$^4$ cells per well in 24-well plates 1 day before start of treatment, were (a) not treated, (b) irradiated with a sub-lethal dose of 4 Gy gamma-irradiation, (c) infected with 0.5 pfu/cell AdΔ24 parental control CRAd, (d) subjected to 4 Gy gamma-irradiation followed by infection with 0.5 pfu/cell AdΔ24 parental control CRAd 1 day later, (e) infected with 0.5 pfu/cell AdΔ24-p53 CRAd according to the invention, or (f) subjected to 4 Gy gamma-irradiation followed by infection with 0.5 pfu/cell AdΔ24-p53 CRAd according to the invention 1 day later. After culture of the cells at 37° C. for 8 days, cell survival was analyzed by WST-1 conversion measurement as in example 2. As can be seen in FIG. 11, irradiation alone decreased cell viability in U87MG and U373MG cells only approximately 10 and 20%, respectively. AdΔ24 treatment alone had a similarly small effect on both cell lines. As seen before, AdΔ24-p53 alone was more effective than AdΔ24 (approximately 40% kill of U87MG and 80% kill of U373MG). Combination treatment of irradiation followed by CRAd infection was more effective than either treatment alone, for both AdΔ24 and AdΔ24-53. Most importantly, the strongest anti-cancer cell efficacy was obtained by combining irradiation with the AdΔ24-p53 CRAd according to the invention (72% and 87% kill of U87MG and U373MG, respectively). Thus, (1) augmented efficacy of combination treatment with CRAds and irradiation was confirmed for the recombinant adenoviruses according to the invention, and (2) the enhanced efficacy of the recombinant adenoviruses according to the invention compared to control adenoviruses was retained in the context of combination treatment with irradiation.

Example 12

Production of Conditionally Replicating Adenoviruses Expressing a Mutant p53 Resistant to Degradation by MDM2

It has been shown previously that a mutant p53 with two amino acid substitutions at positions 14 and 19 retains approximately 50% transactivation activity and 60% adenovirus E1B-55kDa binding affinity, but only approximately 1% MDM2 binding affinity compared to wild type p53 (Lin et al., Genes & Dev. 8 (1994):1235-1246). To construct adenoviruses according to the invention that express this mutant p53, two single nucleotide substitutions that change these amino acids (TSA, L14Q and T>G, F19C) were introduced into the p53 gene on plasmid pABS.4-p53 (see example 1) by PCR-mediated site-directed mutagenesis using Pfu polymerase (Stratagene). First, two PCR amplification products were made using (1) upstream primer 5'-CGTTTCCCGT-TGAATATGGC-3' (SEQ ID NO: 1) and mutation primer 5'-CTGAACATGTTTCCTGACTCTGAGGGGGCTC-3' (SEQ. ID NO: 2) to amplify a first fragment of 651 basepairs; and (2) mutation primer 5'-CCTCAGAGTCAGGAAACAT-GTTCAGACC-3' (SEQ ID NO: 3) and downstream primer 5'-GAAGTCTCATGGAAGCCAGC-3' (SEQ ID NO: 4) to amplify a second fragment of 376 basepairs from pABS.4-p53. Next, the two amplification products were mixed and amplified using the upstream and downstream primers to generate a full length 1002 basepair amplification product containing the two point-mutations. The wildtype SVE-p53 expression cassette from pABS.4-p53 was subcloned into the KpnI and SalI sites in the mutiple cloning site of a pBluescriptSK-derivative with deleted SmaI restriction site to create pBSKASma-p53. The 568 by KpnI/SmaI fragment from the 1002 basepair PCR product encompassing the two mutations was used to replace the corresponding wild type p53 fragment in pBSKASma-p53, creating pBSKASma-p53mut14/19. Correct introduction of the two nucleotide substitutions without any other changes in the p53 gene sequence were confirmed by DNA sequencing (performed at Baseclear in Leiden, the Netherlands). The SVE-p53mut14/19 expression cassette from pBSKASma-p53mut14/19 was cloned into KpnI/SalI-digested pABS.4(Microbix) to create pABS.4-p53mut14/19. Functional p53-specific transactivation capacity by the pABS.4-p53mut14/19 encoded mutant p53 was analyzed by p53-specific transactivation assay. A sequence listing is provided herewith.

SaOS-2 cells (p53 null) were transfected with PG13-Luc (el-Deiry, et al., Cell 75(1993):817-825) together with either pABS.4-p53mut14/19 or pABS.4 as a negative control or pABS.4-p53 as a positive control using Lipofectamin PLUS (Life Technologies, Paisley, UK), according to the method described by the manufacturer. Cells were cultured for 2 days and luciferase activity was measured as in example 3. Two independent experiments were done in triplicate. pABS.4-p53mut14/19 induced luciferase expression 12-fold compared to pABS.4 and pABS.4-p53 induced luciferase expression 58-fold compared to pABS.4. Thus, p53mut14/19 exhibited a partially (20%) retained transactivation capacity compared to wild type p53. Insertion of the SVE-p53mut14/19 expression cassette from pABS.4-p53mut14/19 into pBHG11 and generation of AdΔ24-p53mut14/19 recombinant adenovirus were done using analogous procedures as described in example 1 for AdΔ24-p53. AdΔ24-p53mut14/19 recombinant adenovirus according to the invention is expected to exhibit enhanced oncolytic potency in cancer cells with high MDM2 expression.

The invention claimed is:
1. A replication competent recombinant adenovirus, being capable to replicate and having lytic capacity in target cells, wherein said target cells are hampered in a p53 dependent apoptosis pathway, wherein the adenovirus is a conditionally replicating adenovirus; wherein the adenovirus genome comprises a coding sequence of at least one mammalian restoring factor functional in restoring the p53 apoptosis pathway in said target cells; wherein said coding sequence is operably linked to one or more expression control sequences functional in said target cells, whereby said restoring factor induces accelerated cell lysis and/or a faster release of virus progeny when compared to the recombinant adenovirus lacking said coding sequence, and wherein the virus genome further comprises a gene selected from a gene encoding the adenovirus E1B-19 kDa protein or a functional analog or derivative thereof and a gene encoding the adenovirus E1B-55 kDa protein or a functional analog or derivative thereof.

2. The recombinant virus according to claim 1, wherein the virus is a human adenovirus.

3. The recombinant virus according to claim 1, wherein expression of at least one essential early adenovirus gene is controlled by a tumor-specific promoter.

4. The recombinant virus according to claim 1, wherein the adenovirus is a heterologously trans-complemented adenovirus.

5. The recombinant virus according to claim 1, wherein the virus genome comprises one or more of the genes of the adenovirus E4 region encoding E4 proteins or functional analogues or derivatives thereof.

6. The recombinant virus according to claim 1, wherein the virus genome comprises a gene encoding the adenovirus E1B-55 kDa protein or a functional analog or derivative thereof and a gene encoding the adenovirus E4orf6 protein or functional analogues or derivatives thereof.

7. The recombinant virus according to claim 1, wherein the adenovirus carries a mutation in a E1A region encompassing at least part of the pRb-binding CR2 domain of E1A.

8. The recombinant virus according to claim 1, wherein the restoring factor is p53 protein or a functional analogue or derivative thereof.

9. The recombinant virus according to claim 8, wherein the protein lacks a functional binding domain for a human MdM2 protein.

10. The recombinant virus according to claim 8, wherein the protein is a functional derivative of human p53 with mutated amino acids Leu-14 and Phe-19.

11. The recombinant virus according to claim 1, wherein the target cell is a human cell chosen from the group consisting of cancer cells, arthritic cells, hyperproliferative vascular smooth muscle cells and cells infected with a virus other than said recombinant virus.

12. The recombinant virus according to claim 2, wherein the human adenovirus comprises serotype 5.

13. The recombinant virus according to claim 7, wherein the mutation comprises a deletion encompassing amino acids 122-129 (LTCHEAGF) of SEQ ID NO: 5.

14. The recombinant virus according to claim 1, wherein the restoring factor is chosen from the group consisting of p53, p63, p73, BAX, BAK, BOK/Mtd, BCL-Xs, Noxa/APR, PIDD, p53AIPI, PUMA, KILLER/DR5, Apaf-I, PIG, BID, tBID, BAD, HRK, Bik/Nbk, BLK, mda-7, p14ARF or functional variants, analogues or derivatives thereof.

15. The method for lysing target cells hampered in the p53 dependent apoptosis pathway, comprising the steps of: infecting the said target cells with the replication competent recombinant virus according to claim 1, and replicating said virus within said target cells, further comprising the step of providing, in the virus genome, the coding sequence of at least one restoring factor functional in restoring the p53 dependent apoptosis pathway, said coding sequence being capable to be expressed in the target cells upon infection thereof by said virus.

16. The method according to claim 15, further comprising the step of subjecting said target cells to at least one of irradiation and a toxic chemical compound.

17. The method according to claim 15, wherein said target cells are present in an animal body.

18. A method for treatment of a subject body suffering from a condition involving body cells hampered in a p53 dependent apoptosis pathway, comprising the step of administering to said subject body an effective amount of the replication competent recombinant adenovirus according to claim 1.

19. The method according to claim 18, wherein the condition is associated with uncontrolled cell growth.

20. The method according to claim 19, wherein the condition is chosen from the group consisting of cancer, arthritis, and vascular smooth muscle cell hyperplasia.

* * * * *